United States Patent [19]

Andrews et al.

[11] Patent Number: 5,702,931
[45] Date of Patent: Dec. 30, 1997

[54] MUTAGENESIS METHODS AND COMPOSITIONS

[75] Inventors: William H. Andrews, San Mateo; Michael J. Morser, San Francisco; Laura R. Vilander, Richmond, all of Calif.

[73] Assignee: Berlex Laboratories, Inc., Cedar Knolls, N.J.

[21] Appl. No.: 170,290

[22] PCT Filed: Jul. 1, 1992

[86] PCT No.: PCT/US92/05573

§ 371 Date: Dec. 28, 1993

§ 102(e) Date: Dec. 28, 1993

[87] PCT Pub. No.: WO93/01583

PCT Pub. Date: Jan. 21, 1993

Related U.S. Application Data

[63] Continuation-in-part of Ser. No. 724,237, Jul. 1, 1991, abandoned.

[51] Int. Cl.$^6$ ............ C12N 15/01; C12N 15/11; C12N 15/63; C07H 21/04
[52] U.S. Cl. ............ 435/172.3; 435/91.1; 435/91.4; 435/91.41; 435/91.42; 536/24.33; 536/25.3
[58] Field of Search ............ 435/91.1, 91.4, 435/91.41, 91.42, 172.3; 536/24.33, 25.3

[56] References Cited

U.S. PATENT DOCUMENTS

| | | | |
|---|---|---|---|
| 4,873,192 | 10/1989 | Kunkel | 435/172.3 |
| 5,256,770 | 10/1993 | Glaser et al. | 530/381 |

FOREIGN PATENT DOCUMENTS 0247 647  12/1987  European Pat. Off. .

OTHER PUBLICATIONS

Tsurushita et al., "Site-directed mutagenesis with Escherichia coli DNA polymerase III holoenzyme" Gene (1988) 62: 135–139.

Vandeyar et al., "A simple and rapid method for the selection of oligodeoxynucleotide-directed mutants" Gene (1988) 65:129–133.

Zoller et al., "Oligonucleotide-directed mutagenesis using M-13 derived vectors: an efficient and general procedure for the production of point mutations in any fragment of DNA" Nucleic Acids Research (1982) 10: 6487–6500.

Wallace et al., "Oligonucleotide directed mutagenesis of the human beta-globin gene: a general method for producing specific point mutations in cloned DNA" Nucleic Acids Research (1981) 9:3647–3656.

Zoller et al., "Oligonucleotide-directed mutagenesis: A simple method using two oligonucleotide primers and a single-stranded DNA template" DNA (1984) 3:479–488.

Molecular Biology Reagents 1990, issued 1989 by United States Biochemical Corporation, Cleveland, OH, USA. "T7–GEN(TM) In Vitro Mutagenesis Kit", pp. 125–126.

Technical Manual "Altered Sites II in vitro Mutagenesis System (1994) Promega Corporation".

M. Smith "In Vitro Mutagenesis," Ann. Rev. Genet. (1985) 19:423–462.

M. J. Zoller et al. "Oligonucleotide–Directed Mutagenesis: A Simple Method using Two Oligonucleotide Primers and a Single–Stranded DNA Template," Methods in Enzymology, (1987) vol. 154, pp. 329–350.

W. Kramer et al. "Oligonucleotide–Directed Construction of Mutations via Gapped Duplex DNA," Methods in Enzymology, (1987) vol. 154, pp. 350–367.

T. A. Kunkel, et al. "Rapid and Efficient Site-Specific Mutagenesis without Phenotypic Selection," Methods in Enzymology, (1987) vol. 154, pp. 367–431.

B. Kramer et al. "Different Base/Base Mismatches Are Corrected with Different Efficiencies by the methyl–Directed DNA Mismatch–Repair System of E. coli," Cell, (1987) vol. 38, 879–887, Oct. 1984.

Technical Manual "Altered Sites™ in vitro Mutagenesis System," (1990) Promega Corporation.

R. B. Wallace et al. "Directed Deletion of a Yeast Transfer RNA Intervening Sequence", Science, Sep. 1980, vol. 209, pp. 1396–1400.

D. Young–Sharp et al. "Site–Directed Mutagenesis Using Three Primers and Diagnostic RFLPs In A Single–Dtep Polymerase Chain Reaction," Technique—A Journal of Methods in Cell and Molecular Biology, Jun. 1990, vol. 2, No. 3, pp. 155–162.

J. Liu et al. "An Efficient Method for Introducing Block Mutations Into Specific Regions of a Gene," Biotechniques (1990) 9:738–742.

P. Stanssens et al. "Efficient oligonucleotide–directed construction of mutations in expression vectors by the gapped duplex DNA method using alternating selectable markers," Nucleic Acids Research (1989) 17:4441–4454.

M. Lewis et al. "Efficient site directed in vitro mutagenesis using ampicillin selection," Nucleic Acids Research, (1990) vol. 18, No. 12, pp. 3439–3443.

X. Yang et al. "As efficient site–directed mutagenesis using polymerase chain reaction", Chemical Abstracts, (1992) vol. 116, Abstract No. 52443.

T–J. Shen et al. "A marker–coupled method for site–directed mutagenesis," Gene (1991) 103:73–77.

Primary Examiner—Nancy Degen
Attorney, Agent, or Firm—Wendy L. Washtien

[57] ABSTRACT

Methods and reagents for oligonucleotide-directed mutagenesis of a target nucleic acid are provided. In these methods a mutagenic oligonucleotide introduces a desired mutation at one site and, at a second site, introduces or eliminates a restriction site, allowing one to screen for the desired mutation by restriction analysis. Also provided are vectors and kits for performing such mutagenesis methods.

12 Claims, 24 Drawing Sheets

GGCAGCGCGCAGCGGGCAAGAAGTGTCTGGGCGACGGACAGGAGAGGCTGTCGCCATCGGCGGCGTCCTGTGCCCTCTGCTCCGG aa -1 Signal Sequence
MetLeuGlyValLeuValLeuGly
CACGGCCCTGTCGCAGTGCCCGGCTTTCCCCGGCGCTGCGCGGCGGCCTGGGTAACATGCTTGGGGTCCTTGGC
TACGAACCCCAGGACCAGGAACCG
147

1aa 1 Amino Terminal Domain
AlaLeuAlaLeuAlaGlyLeuGlyPheProAlaProAlaGluProGlnProGlyGlySerGlnCysValGluHisAspCysPhe
GCGCTGGCCCTGGCCGGCCTGGGTTCCCCGCACCCGGCAGAGCCCGGACCCGGGTGGCCAGCCAGTGCGTCGAGCACGACTGCTTC
CGCGACCGGGACCGGGACCCGGAGACCCCAAGGGCCGTGGGCGTCTCGGCCACCGTCGGTCACGCAGCTCGTGCTGACGAAG AlaLeuTyrProGlyProAlaThrPheLeuAsnAlaSerGlnIleCysAspGlyLeuMetThrValArgSer
GCGCTCTACCCGGGCCCCGCGACCTTCCTCAATGCCAGTCAGATCTGCGACGGCCCACCTAATGACAGTGCGTCC
CGCGAGATGGGCCCGGGGCGCTGGAAGGAGTTACGGTCAGTCGGTGGATTACTGTCACGCGAGG SerValAlaAlaAspValIleSerLeuLeuAsnGlyAspGlyValGlyArgArgLeuTrpIleGlyLeuGlnLeu
TCGGTGGCCGATGTCATTTCTCTTGCTACTGAACGGCGACGGCGTTGGCCGCCTCTGATCGGCCTGCAGCTG
AGCCACCGACGGCTACAGTAAAGAACGATGACTTGCCGCTGCCGGCGCCGGAGACCTAGCCGGACGTCGAC ProProGlyCysGlyAspProLysGlyProLeuArgGlyProPheGlnTrpValThrGlyAspAsnThrSerTyrSer
CCACCCGGGCTGCGGCGACCCCAAGGCGCCTCGCGGCCCCTTCCAGTGGGTTACGGGAGACAACAACCAGCTATAGC
GGTGGGCCGACGCCGCTGGGGGTTCGCGGAGCCGGGAAGGTCACCCAATGCCTCTGTTGTTGGTCGATATCG ArgTrpAlaArgLeuAspLeuAsnGlyAlaProLeuCysGlyProLeuCysValAlaValSerAlaAlaAlaThrValPro
AGGTGGGCACGCCTCGACCTCAATGGGGCTCCCCTCTGTGCGGGCCCGTTGTGTCGTGTCTCCGCTGCTGAGGCCACTGTGCCC
TCCACCCGTGCCGAGCTGGAGTTACCCCGAGGGGAGACGCCGGGCAACGCCAGCGACAGAGGCGACGACTCCGGTGACACGGG SerGluProIleTrpGluGlnGluValLysAlaAspPheLeuPheHisProAlaThrCysArg
AGCGAGCCGATCTGGGAGGAGCAGGTGAAGGCCGATGCTTTCTTTGCCCACCCTGCAGG
TCGCTCGGCTAGACCCCTCGTCGTCGACTTCACTTCCGGCTACCGAAGGTGAAGGTCGGTGGACGTCC

FIG. 3a

```
ProLeuAlaValGluProGlyAlaAlaAlaAlaValSerIleThrTyrGlyThrProPheAlaAlaArgGlyAlaAspPhe
CCACTGGCTGTGGAGCCCGGGGCCGCCGCCGCCGTCTCGATCACCTACGGCACCCCGTTCGCGGCCCGGGGAGCGGACTTCGAAG
GGTGACCGACACCTCGGGCCGGCGGCGGCGGCAGAGCTAGTGGATGCCGTGGGGCAAGCGCCGGGCCTCGCCTGAAG

GlnAlaLeuProGlyLeuGlySerSerAlaAlaValAlaProLeuGlyLeuGlnLeuMetCysThrAlaAlaProGlyAlaValGln
CAGGGCGCTGCCCGGTGGGCAGTCCGCGGCGGTGGCTCCCCTCGGCTTACAGTGTAATGTGCACCGCCGCCCCGGAGCGGTCCAG
GTCCGCGACGGGCCACCCGTCAGGCCGCCACCCGTCGAGGGAGCCGAATGTCGATTACACGTGGCGCGGGGCCTGCCAGGTC aa 227    EGF-1
                                ——————

GlyHisTrpAlaArgGluGluValGluAsnGlyGlyAlaProGlyAlaAlaCysSerValGluAsnGlyGlyCysSerHisAlaCysAsnAlaIlePro
GGGCACTGGGCCCAGGAGGCGGTGGAGAACGGGGCTCCAGGCGCTGCCTGCAGCGTGGAGAACGGCGGTGTGCGACGAGTCCTGC
CCCGTGACCCGGTCCTCCGCCACCTCCGCCGCAATGGCCGCGGGTCCGCCGGCCAGCGTCGCACCCTTGCCGCCCACGTTACGCTAGGA aa 262
                                                                        ——————

GlyAlaProArgCysGlnCysProAlaGlyLeuGlnAlaLeuAlaAspGlyArgSerCysThrAlaSerAlaThrGlnSerCys
GGGCTCCCCCGTTGCCAGTGCCCAGCCGGCCTTGCAGGCGCTGGCAGACGGCCGCTCCTGCACCGCATCCGCGACGCAGTCCTGC
CCCGAGGGGGCAACGGTCACGGTCAGGTCACGGTGCCCCGAGGACGTGGCGTAGGCGTGCTGCCGGAAGTCAGGACG
EGF-2 aa 270
                                                                        ——————

AsnAspLeuCysGluHisPheCysValProAsnProAspGlnProGlySerTyrSerCysMetCysGluThrGlyTyrArgLeu
AACGACCTCTGCGAGCACTTCTGCGTTCCCAACCCGGACCAGCCGGGCTCCTACTCGTGCATGTGCGAGACGGGCTACCGGCTG
TTGCTGGAGACGCTCGTGAAGACGCAAGGGTTGGGCCTGGTCGGCCCGAGGATGAGCACGTACACGCTCTGCCCGATGGCCGAC aa 305     aa 311    EGF-3
                                                                ——————     ——————

AlaAlaAlaAspGlnHisArgCysGluAspValAspAspCysIleLeuGluProCysProGlnArgCysValAsnThrGln
GCGGCCGCCGACCAACACCGGTGCGAGGACGTGGATGACTGCATACTGGAGCCCTGTCCGCAGCGCTGTGTCAACACACAG
CGCCGGCGGCTGGTTGTGGCCACGCTCCTGCACCTACTGACGTATGACCTCGGGACAGGCGTCGCGACACAGTTGTGTC
```

O-Linked Glycosylation Domain (starts at aa 463)
------------------------------------------------
ValAspGlyGlyAspSerGlyGluProProThrLeuThrProProGlySerThrProProAlaValGlyLeu
GTGGACGGTGGCGACAGCGGGCTCTGGGAGCCCCGACCCCGGCTCCCACCTTGACTCCTCCGGCCGTGGGGCTC
CACCTGCCACCGCTGTCGCCGAGAACGCGCTCGGGGGCGTGGGGGCTGCGGAGGTGGAACTGAGGAGGCCACCCCGAG aa 497    Stop Transfer Sequence
-------|                                                                   aa 520|
ValHisSerGlyLeuLeuLeuIleGlyIleSerIleAlaSerLeuValValAlaLeuAlaLeuLeuCysHisLeuArg
GTGCATTCGGGCTTGCTCATAGGCATCTCCATCGCGAGCCTTGTCGTGGCCCTTGCGCTCCTCTGCCACCTGCGC
CACGTAAGCCCGAACGAGTATCCGTAGAGGTAGCGCTCGGACACGGGGACAACCGCGAAAACGCGAGGAGACGGTGGACGCG Cytoplasmic Domain (starts at aa 521)
LysLysGlnGlyAlaAlaArgAlaAlaLysMetGluTyrLysCysAlaAlaProSerLysGluValValLeuGlnHisValArgThr
AAGAAGCAGGGCGCCGCGCGGGCCGCCAAGATGGAGTACAAGTGCGCCGCCCCTTCAAGGAGGTGGTGCAGCACGTGCGGACC
TTCTTCGTCCCGCGGCGCCCGGCGGTTCTACCTCATGTTCACGCGGCGGGGAAGTTCCTCCATCACGACGTCGTGCACGCCTGG aa 557
|
GluArgThrProGlnArgLeu0P
GAGCGGACGCCGCAGAGACTCTGAGCGGCCTCCGTCCGTCCAGGAGCCTGGCTCTGTGCCTCCTCACCCCCAGCTT
CTCGCCTGCGGCGTCTCTGAGACTCGCCGGAGGCAGGTCCTCGGACCGAGACACGGAGGAGTGGGGGTCGAA

TGCTACCAAAGCACCTTAGCTGGCATTACAGCTGGAGAAGACCCTCCCCGACACCCCCAAGCTGTTTCTTCTATTC

FIG. 3d

Primers for replacing the Methionine at aa 291

Native Sequence

```
 ProAspGlnProGlySerTyrSerCysMetCysGluThrGlyTyrArgLeuAlaAla
CCCCGACCAGCCGGGCTCCTACTCGTGCATGTGCGAGACCGGCTACCGGCTGGCGGCCG
```

Mutant Primer 1580

```
                              Leu
CCCCGACCAGCCGGGCTCCTACAGCTGCCTGTGCGAGACCGGCTACCGGCTGGCGGCCG
                      ^
                     PvuII
```

Mutant Primer 1581

```
                           Gln
      CAGCCGGGCTCCTACTCGTGCCAGTGCGAGACTGGCTACCGGCTGGCGGCCG
                           ^
                          XcmI
```

Mutant Primer 1582

```
                             Ala
CCCCGACCAGCCGGGCTCCTACTCGTGCGCATGCGAGACCGGCTACCGGCTGGCGGCCG
                           ^ ^
                          FspI SphI
```

Primers for replacing the Methionine at aa 388

Native Sequence

```
 ProHisGluProHisArgCysGlnMetPheCysAsnGlnThrAlaCysProAla
CCCCACGAGCCGCACAGGTGCCAGATGTTTTGCAACCAGACTGCCTGTCCAGCCG
```

Mutant Primer 1573

```
                         Leu
CCCCACGAGCCGCACAGGTGCCAGCTGTTTTGCAACCAGACTGCCTGTCCAGCCG
                        ^
                      PvuII
```

Mutant Primer 1583

```
                        Gln
CCCCACGAGCCGCACAGGTGTCAACAGTTTTGCAACCAGACTGCCTGTCCAGCCG
                     ^
                   HincII
```

Mutant Primer 1584

```
                        Ala
CCCCACGAGCCGCACAGGTGCCAGGCCTTTTGCAACCAGACTGCCTGTCCAGCCG
                       ^
                      StuI
```

FIG. 4

MUTAGENESIS METHODS AND COMPOSITIONS

This application is the U.S. national stage of international application number PCT/US92/05573, filed Jul. 1, 1992, which is a continuation-in-part of U.S. application Ser. No. 07/724,237, filed Jul. 1, 1991, and now abandoned.

BACKGROUND OF THE INVENTION

1. Field of the Invention

The present invention relates generally to the oligonucleotide-directed mutagenesis of nucleic acids.

Oligonucleotide-directed mutagenesis is a valuable tool for the study of DNA function and protein structure and function, having become the method of choice to introduce predetermined structural changes into DNA. Such manipulation permits the alteration of a DNA sequence in order to determine its function, or may permit the production of reagents with commercial or medical significance. A number of different methods have been reported. See, inter alia, M. Smith, Ann. Rev. Genet. (1985) 19:423 for a review; and Section IV, Chapters 17–21, Meth. Enzymol. (1987) 154:329–414, both incorporated herein by reference.

Oligonucleotide-directed mutagenesis is accomplished by annealing to single-stranded DNA (ssDNA) a synthetic oligonucleotide which is complementary to the single-stranded template, except for an internal mismatch which directs the required change (point mutation, multiple mutation, insertion or deletion), resulting in the formation of a mutant-wild-type heteroduplex. There have been several adaptations of this basic concept. In most methods, following hybridization with the single-stranded target DNA, the oligonucleotide is extended with DNA polymerase to create a double-stranded structure. It is possible, in a "gapped duplex" approach, to forego the extension of the oligonucleotide with polymerase (W. Kramer and H.-J. Fritz, Meth. Enzymol. 154:350 (1987), incorporated herein by reference). In either case, the double-stranded DNA is then transformed into an E. coli host.

Theoretically, the yield of mutants using this procedure should be 50% due to the semi-conservative mode of DNA replication. That is, as cells transformed with the double-stranded heteroduplex DNA replicate each of the strands, one-half of their progeny will theoretically contain either wild-type or mutated DNA. In practice, however, the mutant yield may be much lower, often only a few percent or less. This is assumed to be due to such factors as incomplete in vitro polymerization, primer displacement by the DNA polymerase used in the fill-in reaction, and in vivo host-directed mismatch repair mechanisms which favor repair of the unmethylated newly synthesized DNA strand (B. Kramer et al., Cell 38:879 (1984)). Several methods have been described which increase the likelihood of obtaining the desired mutant, either selecting against wild-type DNA (e.g., T. Kunkel, U.S. Pat. No. 4,873,192 (1989), incorporated herein by reference), or for the mutated DNA (e.g., "Altered Sites (TM) In Vitro Mutagenesis System Technical Manual", Promega Corporation (1990), incorporated herein by reference). A commercial kit for polymerase III site-directed mutagenesis is commercially available from Stratagene, La Jolla, Calif. under the tradename MUTA-TOR™ (Catalogue #200500).

The most general method for mutant screening is by hybridizing DNA from cells transformed with the double-stranded mutagenesis product with a 5'-labeled mutagenic oligonucleotide (R. Wallace et al., Science 209:1396 (1980), incorporated herein by reference). Under nonstringent conditions (e.g., room temperature wash) the probe hybridizes both to the mutant DNA to which it is perfectly matched and also to wild-type DNA to which it is mismatched. By increasing the stringency of washing (e.g., by elevating the temperature) the mutagenic oligonucleotide can be selectively dissociated from wild-type DNA, leaving it bound to mutant DNA. DNA is then prepared and sequenced to verify the mutation. If one employs oligonucleotide-directed mutagenesis methods which result in a high proportion of transformed cells bearing mutant DNA, one can often use sequencing itself as a mutant screen.

Although oligonucleotide-directed mutagenesis has become a valuable tool in the hand of biologists, it remains time-consuming and expensive to perform, particularly when large numbers of mutations or multiple mutations on the same template are required. For example, in protein structure-function studies it may be necessary to replace one or several amino acids in a protein with every other amino acid in order to determine the importance of that amino acid to the function of the protein, or to seek amino acids replacements which would provide a desired function (e.g., increased or decreased binding, increased stability, etc.). Conventional oligonucleotide-directed mutagenesis, in most cases, requires verification of mutants by hybridization and/or sequencing. Furthermore, in order to introduce a sequence alteration into a template which has been previously mutagenized, it may be necessary to subclone the previously mutagenized template into a new vector sequence.

It would therefore be desirable to provide methods and compositions for oligonucleotide-directed mutagenesis of nucleic acids which facilitate screening to identify mutants and in particular which permit one to generate multiple mutations or sequential mutagenesis of a single site within the nucleic acid without the need to subclone. Preferably, the methods will allow screening of the mutants without hybridization or sequencing. Especially for applications requiring the generation of a large number of site-specific mutations, oligonucleotide-directed mutagenesis methods are required which require far less time, effort and expense than those previously described.

SUMMARY OF THE INVENTION

The present invention provides a significant improvement over previously described oligonucleotide-directed mutagenesis efforts, addressing these and other needs, providing methods and kits for rapidly and easily site-specifically modifying a target nucleic acid, methods especially well suited to introducing multiple mutations at one or several positions on the target nucleic acid.

Each of these methods employs one or more mutagenic oligonucleotides which are capable of introducing a desired change, whether a nucleotide replacement or the insertion or deletion of one or more nucleotides, in a target nucleic acid. At the same time, each mutagenic oligonucleotide also introduces or, less commonly removes, a restriction site at another position, allowing one to screen for the desired mutation(s) by restriction analysis. Since the same oligonucleotide introduces both the desired mutation and alters the restriction pattern, one need not verify the presence of the desired mutation by hybridization and/or sequencing.

One embodiment of the present invention is a method for site-specifically modifying a nucleic acid construct having a target sequence, comprising the steps of annealing to a single-stranded form of the nucleic acid construct an oligonucleotide having a sequence substantially complementary to a portion of the nucleic acid construct and capable of changing a nucleotide at one position within the target sequence, and also capable of introducing or removing a restriction site at a different position of the nucleic acid construct. The product of this annealing is used to transform a host cell. Progeny of transformed host cells containing a nucleic acid construct having the desired mutation are easily identified by restriction analysis.

In another embodiment of the present invention, methods are provided in which the nucleic acid construct has, in addition to the target sequence, a sequence encoding a screenable or, preferably, selectable marker. In such methods, in addition to an oligonucleotide capable of introducing a desired mutation in a target sequence, a second oligonucleotide capable of introducing a change in the marker sequence and thus alter its activity in a detectable manner. By screening or selecting for transformed cells displaying this altered marker activity (e.g., by selecting for antibiotic resistant cells), one is highly likely to find cells having a target sequence with the desired mutation(s) after screening a small number of such cells by restriction analysis.

Another embodiment is a "dual marker system" in which the nucleic acid construct has, in addition to the target sequence, two sequences encoding different marker activities. Such a system provides an especially powerful means for performing sequential mutagenesis of one or more nucleotides of a target sequence. In the first round, one mutates the target sequence and the sequences and activities of both markers as described above. In the second round, one further mutates the target sequence and restores the original marker sequences and activities. One may continue for as many rounds as necessary to performed the desired changes in the target sequence. As an example, one may employ as markers a first sequence conferring resistance to antibiotic A and a second sequence, which is mutated, but which, when restored to "wild-type sequence", confers resistance to antibiotic B. In the first round, cells are selected for resistance to B (and screened for sensitivity to A). In the second round, the situation is reversed. Subsequent rounds cycle back and forth between the two patterns of antibiotic resistance. Significantly, there is no need to subclone the target sequence for each mutagenesis round.

In these embodiments of the present invention, if the target sequence encodes a polypeptide, the mutagenic oligonucleotide introduces the desired change, typically replacement, insertion or deletion of one or more amino acids, while at the same time introducing or removing a restriction site, preferably without changing an amino acid of the polypeptide. The target sequence encoding a polypeptide may be operably linked to a promoter, as in an expression vector.

These methods may optionally comprise the steps of extending the oligonucleotide(s) with a DNA polymerase and/or add a DNA ligase.

The present invention also provides kits for performing oligonucleotide-directed mutagenesis by any of the methods described above, comprising:

(a) a nucleic acid construct comprising an origin of replication, a restriction site for inserting target sequences, a first marker sequence encoding a first marker activity, and a second marker sequence encoding a second marker activity; and (b) oligonucleotides having sequences substantially complementary to a portion of the nucleic acid construct and capable of introducing a change in the first and second marker sequences, thus significantly alters marker activities.

These kits may further comprise:

(a) additional oligonucleotides, as described above, capable of restoring first and second marker sequences and activities; and/or (b) a DNA polymerase, deoxyribonucleotides, and a buffer suitable for the activity of the DNA polymerase.

In addition, mutagenesis/selection vectors suitable for use with the methods of the present invention are provided, and may be included with the above mentioned kits.

BRIEF DESCRIPTION OF THE DRAWINGS

FIGS. 3A–3D (SEQ ID NOS: 53 and 54) listings of the nucleotide and amino acid sequences of native human thrombomodulin showing the six EGF-like domains regions of native human thrombomodulin.

FIG. 4 (SEQ ID NOS: 55, 56, 57, 58, 59, 60, 61, 29, 62, and 63) includes the nucleotide sequences for the primers used for site-directed introduction of restriction sites and amino acid substitutions described in the Experimental section.

FIG. 5 also describes four oligonucleotides useful in mutagenesis/selection: COD2461, which changes Amps to AmpR (i.e., ampicillin sensitivity to ampicillin resistance) and creates an FspI site; COD1941, which changes CatR to Cats (i.e., chloramphenicol resistance to chloramphenicol sensitivity) and creates a BspHI site; COD1632, which changes AmpR to Amps and creates an XcmI site; and COD1940, which changes Cats to CatR and creates an AvaI site.

DETAILED DESCRIPTION OF THE PREFERRED EMBODIMENTS

Figure 1:
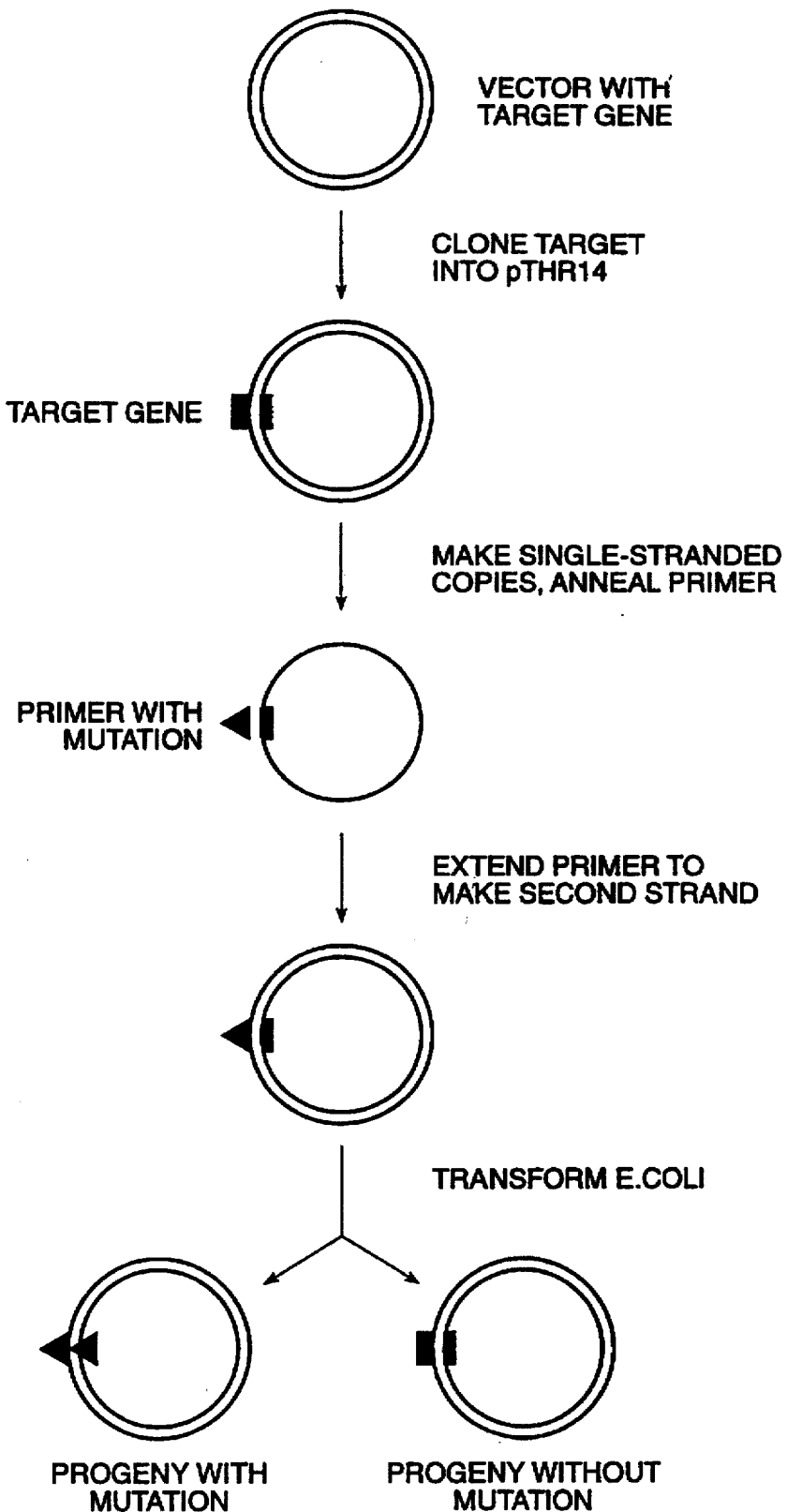
FIG. 1 schematically illustrates the method of site directed mutagenesis used to create the oxidation resistant TM analogs described by this invention.

The present invention provides methods for rapidly and easily performing oligonucleotide-directed mutagenesis of a nucleic acid construct having a target sequence to be mutated. Multiple mutations may be performed on a single such target sequence simultaneously and/or sequentially, and more than one such target sequence may be included on a single construct. The nucleic acid constructs will comprise or be suitable for incorporation into a self-replicating, preferably extrachromosomal element capable of being maintained in a suitable host. The constructs will usually contain one or more marker sequences to permit ready identification or selection of hosts cells containing a mutated target sequence. The cloned target sequences will usually be protein-coding sequences, but may also include noncoding sequences as described below.

Nucleic Acid Constructs

Nucleic acid constructs useful in the practice of the present invention will facilitate the cloning of the target sequence, i.e., production of usable quantities of the nucleic acid, and will usually be able to direct the expression of a polypeptide encoded by the target sequence. The nucleic acid constructs will contain different components depending upon the function they are to perform as well as the host cell into which they are introduced.

Commonly, the nucleic acid constructs will be DNA expression vectors, incorporating target sequences encoding a polypeptide, suitable for replication in a unicellular host, such as bacteria or possibly a yeast. Alternatively, they may be intended for introduction into a cultured mammalian or plant or other eukaryotic cell lines. Such vectors will usually include a replication system recognized by the host, including an origin of replication or autonomously replicating sequence (ARS), a sequence or sequences encoding polypeptide products, and transcription and translational initiation regulatory sequences operably linked to the polypeptide encoding sequences. The transcriptional regulatory sequences may include a heterologous enhancer and/or promoter and necessary processing information sites, such as ribosome-binding sites, RNA splice sites, polyadenylation sites, transcriptional terminator sequences and mRNA stabilizing sequences, all of which are recognized by the host. Such expression vectors may also include secretion signals from secreted polypeptides of the same or related species, which allow the protein to cross and lodge in cell membranes, and thus attain its functional topology.

While such expression vectors may replicate autonomously, they may, in the alternative, replicate by being inserted into the genome of the host cell, by methods well known in the art.

It will be appreciated that the target sequence within such nucleic acid constructs may be other than the polypeptide encoding sequences. For example, it may be desirable to alter sequences controlling transcription or translation or the processing of nucleic acids or proteins; on origins of replication; or to remove introns from a polypeptide-encoding sequence.

The selection of an appropriate promoter will depend upon the host, but for bacterial hosts, bacterial promoters such as the trp, lac and phage promoters, tRNA promoters and glycolytic enzyme promoters are known and commonly used. See, Sambrook et al., *Molecular Cloning: A Laboratory Manual* (2nd ed.), Vols. 1-3, Cold Spring Harbor Laboratory, (1989), incorporated herein by reference. Useful yeast promoters include the promoter regions for metallothionein; 3-phosphoglycerate kinase or other glycolytic enzymes such as enolase, glyceraldehyde-3-phosphate dehydrogenase; enzymes responsible for maltose and galactose utilization; and others. Suitable vectors and promoters for use in yeast expression are further described in R. Hitzeman et al., EP 73,657A, incorporated herein by reference. Appropriate non-native mammalian promoters might include the early and late promoters of SV40 or promoters derived from mouse mammary tumor virus, arian sarcoma viruses, adenovirus II, bovine papilloma virus or polyoma virus, among others. Examples of workable combinations of cell lines and expression vectors are described in Sambrook et al. (1989); see also, Metzger et al. *Nature* 334:31 (1989), incorporated herein by reference.

A nucleic acid is operably linked when it is placed into a functional relationship with another nucleic acid sequence. For instance, a promoter or enhancer is operably linked to a sequence encoding a polypeptide if it affects the transcription of the sequence. Generally, operably linked means that the DNA sequences being linked are contiguous and, where necessary to join two protein coding regions, contiguous and in reading frame. Subcloning nucleic acid sequences encoding polypeptides into vectors and other techniques for nucleic acid manipulation are described generally, for example in Sambrook et al., *Molecular Cloning: A Laboratory Manual* (2nd ed.), Vols. 1-3, Cold Spring Harbor Laboratory, (1989) or *Current Protocols in Molecular Biology*, F. Ausubel et al., ed. Greene Publishing and Wiley-Interscience, New York (1987), which are incorporated herein by reference.

Vectors

Preferred vectors for cloning polypeptide-encoding sequences and performing the mutagenesis methods of the present invention will contain two antibiotic markers as described above, and additional features, including:

(1) An origin of replication (ori) suitable for propagation of the vector in prokaryotic cells, preferably *Escherichia coli*, such as the ColE1 ori. High copy number vectors are preferred, such as those based on the pUC vectors, which lack sequences from the ColE1 replicon which depress copy number, since their DNA is more abundant and thus more easily purified from the host cell. High vector copy number vectors also allow for correspondingly higher levels of expression of proteins encoded by sequences inserted into the the vector.

(2) An origin of replication allowing the convenient production of a single stranded form of the vector sequence, such as ori obtained from such single stranded DNA phage as M13 or f1.

(3) A polylinker for easily inserting into the vector a variety of restriction fragments. The polylinker will preferably be situated within the lacZ gene, allowing for blue/white screening for insertions into the polylinker. A series of vectors having the polylinker in all three reading frames and in both orientations with reference to the lacZ gene provides maximum cloning flexibility.

Additional desirable features may include: dual opposed phage promoter sequences flanking the polylinker (e.g., the SP6 or T7 promoters) and capable of directing in vitro the production of RNA transcripts comprising inserted target sequences; convenient binding sites for oligonucleotide sequencing primers (e.g., pUC/M13 forward and/or reverse sequencing primers) flanking the polylinker for convenient sequencing of the inserted target sequence by the chain termination method; or other features as will be apparent to those skilled in the art.

The pSELECT(TM)-1 vector (Promega Corp.) incorporates many of these features and is useful for the mutagenesis methods of the present invention. We have constructed vectors, shown in FIGS. 5 through 10, employing an ampicillin resistance gene rendered sensitive by a different mutation than that in the ampicillin resistance gene of pSELECT (TM)1, resulting in a measurably higher copy number. In these vectors an antibiotic resistance marker other than the tetracycline resistance gene present on pSELECT(TM)1, e.g. chloramphenicol acetyl transferase (CAT), is also employed, since some desirable *E. coli* host strains (e.g., BMHmutS) are already resistant to tetracycline.

Also useful for the methods of the present invention are vectors which allow one not only to mutagenize a target sequence and screen or select for the mutated sequence as provided by the mutagenesis methods of the present invention, but also to express proteins encoded by a mutated sequence in eukaryotic cells. The use of such vectors provides significant time savings in some cases, allowing one to express a mutated protein coding sequence and directly screen or select for a mutant phenotype without the need to isolate the mutated target sequence from a mutagenesis vector and subclone the sequence into an expression vector.

Eukaryotic expression vectors also will include markers appropriate for selecting eukaryotic cells into which such vectors have been introduced, as discussed infra. For example, mammalian mutagenesis/expression vectors may employ the myeloproliferative sarcoma virus (MPSV) promoter, the SV40 early promoter, or human metallothionein II promoter to drive expression of the cloned target sequence. Appropriate markers for selection of the vector in mammalian cells include puromycin-N-acetyl-transferase (Pac), which confers puromycin resistance; dihydrofolate reductase (DHFR), which confers methotrexate resistance; or the hygromycin B resistance gene (hyg B). Such vectors may be so designed as to be used for either transient or stable expression of cloned target sequences. For transient expression, such vectors will preferably include, e.g., origins of replication which function in the host cells of interest (e.g., the SV40 origin of replication for stable expression in mammalian cells). For stable expression, markers which are selectable and, preferably, amplifiable (e.g., dihydrofolate reductase, DHFR), will be required.

Baculovirus mutagenesis/expression vectors may also be useful. In such vectors the polyhedrin promoter, for example, may drive the expression in insect cells of target sequences cloned in the polylinker. Ampicillin and chloramphenicol resistance genes may be used as dual selectable markers.

It will be readily apparent to one skilled in the art that other promoters and markers which are well known in the art will be useful for expression and selection in various eukaryotic (e.g., yeast, insect, amphibian, avian, mammalian) cells. In addition, it would be obvious to one skilled in the art to employ site-directed mutagenesis or other well known techniques to alter the cloning sites of the vectors described in the present application so that the cloning site into which a target sequence is cloned is provided in all three reading frames to facilitate the expression of target sequences encoding a polypeptides.

Marker sequences

Expression and cloning vectors according to the present invention will contain one or more screenable and/or selectable marker sequences. A screenable marker sequence encodes a protein whose activity is easily detected, allowing cells expressing such a marker to be readily identified. Such markers include, for example, β-galactosidase, β-glucuronidase, and luciferase. A selectable marker is a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for Bacilli. The choice of the proper selectable marker will depend on the host cell, and appropriate screenable and selectable markers for different hosts are well known in the art.

A preferred embodiment for the present invention is a two antibiotic marker system. The first selectable antibiotic marker is inoperative due to a insertion, deletion or replacement at a single site in the marker sequence; the second selectable antibiotic marker is operative. During a mutagenesis of a polypeptide encoding sequence, in addition to the oligonucleotide responsible for that mutation, one also employs an oligonucleotide which mutates the first marker to make it operable (i.e., restores its wild-type sequence and activity) and another oligonucleotide which makes the second marker inoperable by replacing, inserting or deleting one or more nucleotides of the nucleic acid sequence encoding that second marker. One can select for transformed cells having nucleic acids arising from a mutated strand by growing them in the presence of an antibiotic for which the first marker gives the cells resistance. If one wishes to further mutate that polypeptide encoding sequence, one also mutates the first marker to make it inoperable, and the second marker to make it operable, thus "cycling back" to the original sequence for each marker without the necessity of subcloning the polypeptide encoding sequence into a new vector. Such a system makes much easier and faster sequential mutations of the same polypeptide-encoding sequence.

Oligonucleotides

An oligonucleotide is a single-stranded DNA, typically prepared by synthetic means. Those oligonucleotides employed in the present invention preferably being 10 to 100, more preferably 16 to 40 nucleotides in length, although oligonucleotides of different length may be appropriate. For example, in order to mutate more than one amino acid in a peptide, a longer oligonucleotide may be required in order to maintain sufficiently long regions of complimentarily to assure proper annealing of the oligonucleotide to the single-stranded form of the target nucleic acid to be mutated. Longer oligonucleotides will also be appropriate if one chooses to perform a "gapped duplex DNA" approach (Kramer and Fritz, *Meth. Enzymol.* (1987) 154:350–367, incorporated herein by reference).

Suitable oligonucleotides may be prepared by the phosphoramidite method described by Beaucage and Carruthers, *Tetra. Letts.* 22:1859–1862 (1981), or by the triester method according to Matteucci, et al., *J. Am. Chem. Soc.*, 103:3185 (1981), both incorporated herein by reference, or by other methods such as commercial automated oligonucleotide synthesizers.

The methods of the present invention, in one embodiment, employ oligonucleotides having a sequence substantially complementary to a portion of the target sequence (thus allowing the oligonucleotide to anneal to the template) and capable of (a) changing a nucleotide of that target sequence, and (b) introducing or removing a restriction site elsewhere on the nucleic acid construct ("mutagenic oligonucleotides").

In a particular embodiment, the target sequence encodes a polypeptide. In this case, the introduction or removal of a restriction site by the mutagenic oligonucleotide is accomplished without changing an amino acid of that polypeptide-encoding sequence. In all cases, the sequence of these mutagenic oligonucleotides is ultimately incorporated into the mutated nucleic acid.

The mutagenic oligonucleotide will be capable of changing one or more nucleotides at a precise position or positions within the nucleic acid construct, i.e., introduce a site-specific modification(s) resulting from one or more mismatches in the nucleic acid sequence. If the target sequence encodes a polypeptide, incorporating the sequence of the mutagenic oligonucleotide will usually result in an amino acid replacement or the insertion or deletion of one or more amino acids. As can be readily appreciated by those skilled in the art, one nucleotide base change in a nucleic acid may be sufficient to give a desired change in the amino acid sequence it encodes, although more than one such base change may be necessary. In addition, each oligonucleotide may be used to change more than one amino acid, or to truncate a polypeptide by introducing a stop codon.

Those same mutagenic oligonucleotides are capable of introducing or removing a restriction site from the nucleic acid construct without changing an amino acid of said polypeptide. This restriction site change provides a reliable diagnostic for the presence of the desired polypeptide sequence change described above, eliminating the need to verify the presence of this polypeptide sequence change by sequencing. The restriction site may be located within or, less usually, outside the target sequence. By diagnostic restriction digests of the mutagenesis products, one can quickly and easily screen for a multitude of such changes in one or several nucleic acid constructs. While one skilled in the art will be capable of designing oligonucleotides of this type, incorporating principles such as degeneracy in the genetic code, codon frequency information, and useful restriction site sequences, assistance is available from such computer programs as GeneWorks, Intelligenetics, Palo Alto.

In addition to these oligonucleotides, the methods of the present invention optionally employ oligonucleotides having a sequence substantially complementary to a portion of one or more marker sequences, as described above, and capable of introducing a change in the marker sequence which significantly alters marker activity (e.g., antibiotic resistance). Nucleotide replacements, commonly those encoding amino acid replacements or truncated marker proteins; insertions; or deletions may be introduced into marker sequences by the methods of the present invention. A preferred embodiment of the present invention is the use of a dual marker system, especially, although not limited to, one involving two antibiotic resistance markers, a first, operable (i.e., wild-type, antibiotic resistant) marker and a second inoperable (i.e., mutant, antibiotic sensitive) marker. Such a system is especially useful in performing multiple rounds of mutagenesis on a single target. In the first round, one oligonucleotide is responsible for mutating the first marker to antibiotic sensitivity; another oligonucleotide mutates the second marker to antibiotic resistance. The next round reverses the process, mutating the markers to restore their original status. This cycle may be repeated as often as desired. In each mutagenesis round, one screens or, preferably, selects for cells expressing the marker mutated to confer antibiotic resistance, and can test cells so selected for sensitivity to other marker. The target DNA in such cell probably also contains the desired mutation in a polypeptide-encoding region, obtained as described above. The presence of this desired mutation is easily screened for by diagnostic restriction digests, which reliably indicate the presence of the desired mutation since an altered restriction site and desired mutation are generated by the same mutagenic oligonucleotide.

An oligonucleotide is substantially complementary to a portion or region of the nucleic acid construct when it will anneal only to a single desired position on the construct under conditions determined as described below. Such an oligonucleotide will preferably contain one, more preferably containing more than one, region of eight or more consecutive nucleotides and have one or more nucleotides at the 3'-end of the oligonucleotide displaying perfect complementarity (i.e., base pairing to a single stranded region of a target nucleic acid), although longer oligonucleotides (e.g., more than 20 nucleotides) may anneal with the desired specificity with no such region of consecutive nucleotides with perfect complementarity. Proper annealing conditions depend, for example, upon an oligonucleotide's length, base composition, and the number of mismatches and their position on an oligonucleotide, and must often be determined empirically. For discussions of oligonucleotide design and annealing conditions, see, for example in Sambrook et al., *Molecular Cloning: A Laboratory Manual* (2nd ed.), Vols. 1-3, Cold Spring Harbor Laboratory, (1989) or *Current Protocols in Molecular Biology*, F. Ausubel et al., ed. Greene publishing and Wiley-Interscience, New York (1987), which are incorporated herein by reference.

It will be readily appreciated that one may employ multiple mutagenic oligonucleotides to mutate several sites on a polypeptide encoded by a target nucleic acid. One may, in this circumstance, obtain a majority of the mutations desired, but fail to obtain all the desired mutations in a single mutagenesis round. One can readily obtain the remaining mutations by sequential mutations of the same template by employing, for instance, the dual marker system described above, without subcloning the target nucleic acid to be mutated. The time and effort required to generate multiple mutations in a target nucleic acid is dramatically simplified by the use of the methods of the present invention.

After annealing of the oligonucleotide to a single stranded form of the nucleic acid construct, the oligonucleotide may be extended by a DNA polymerase. T4 DNA polymerase is preferred to Klenow fragment of DNA polymerase I for this purpose, because it does not strand displace and therefore does not displace the oligonucleotides (Y. Masamune and C. Richardson, *J. Biol. Chem.* (1971) 246:2692; J. Nossal, *J. Biol. Chem.* (1974) 249:5668; both incorporated herein by reference). One may increase the number of mutants by using phosphorylated oligonucleotides, although for convenience sake, this step may be omitted. Custom phosphorylated oligonucleotides may be obtained from several vendors or may be made by protocols described in Sambrook et al., *Molecular Cloning: A Laboratory Manual* (2nd ed.), Vols. 1-3, Cold Spring Harbor Laboratory, (1989) or *Current Protocols in Molecular Biology*, F. Ausubel et al., ed. Greene publishing and Wiley-Interscience, New York (1987), which are incorporated herein by reference. A nick remaining after extension may be sealed with DNA ligase, although this step is optional.

It will often be the case that the nucleic acid construct one wishes to modify naturally assumes a single stranded form for at least part of their life cycle, as is true, for instance, in the case of single stranded DNA phage like M13 or f1. There are a number of multi-functional plasmid vectors (often called "phagemid" vectors) appropriate for use in the present invention which have M13 or f1 origins of replication. When, for instance, appropriate host cells (e.g., JM109) containing a plasmid having an M13 origin of replication are infected with wild-type M13 phage, single stranded forms of the plasmid are generated. Alternatively, double stranded plasmids containing a polypeptide-encoding region to be mutated may be denatured by various means well known to those skilled in the art, such as denaturation by alkali or boiling, to produce a single stranded form of the target DNA to which an oligonucleotide may anneal (See, Sambrook et al., *Molecular Cloning: A Laboratory Manual* (2nd ed.), Vols. 1-3, Cold Spring Harbor Laboratory, (1989) or *Current Protocols in Molecular Biology*, F. Ausubel et al., ed. Greene publishing and Wiley-Interscience, New York (1987), which are incorporated herein by reference).

A partially double stranded nucleic acid is formed when an oligonucleotide is annealed to a single stranded form of a target nucleic acid. A substantially double stranded nucleic acid exists when more than 50%, more preferably 90%, and most preferably 95% or more of the target nucleic acid is annealed to one or more oligonucleotides and/or the product of their extension with a polymerase, not including those regions which will be deleted as a result of the mutagenesis. Mutagenesis of many sites on the same protein-encoding sequence It is understood that one may employ the method of the present invention to mutate many sites on a polypeptide-encoding sequence through the use of a corresponding number of mutagenic oligonucleotides. The use of T4 DNA polymerase, which does not displace the mutagenic oligonucleotides, will preferably be used in such mutageneses, where extension of the oligonucleotides is desired. The method of the present invention has been successfully employed to simultaneously mutate as many as nine sites in a single polypeptide. It may be the case that one attempts such a mutation of numerous sites with a large number of oligonucleotides and obtains mutations at some, but not all the desired positions. It will be readily apparent, after diagnostic restriction digests, which sites remain to be mutated. One may then simply perform a secondary mutagenesis of the remaining sites using the appropriate mutagenic oligonucleotides, a matter simplified by the dual marker system described above.

Transformation of host cells

The partially or substantially double-stranded nucleic acids produced after annealing to the target nucleic acid the oligonucleotides described above, which may be extended by DNA polymerase, can be introduced directly into host cells by well known methods, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); microinjection; and other methods. See generally, Sambrook et al., (1989) and F. Ausubel et al. (ed.), (1987), both incorporated herein by reference. The cells into which have been introduced nucleic acids described above are meant to also include the progeny of such cells.

Preferred host cells for transformation are repair minus E. coli strains (e.g., mut S strains such as BMH 71-18 mut S), which suppress in vivo mismatch repair (B. Kramer et al., Cell (1984) 38:879; R. Zell and H. Fritz, EMBO J. (1987) 6:1809; both incorporated herein by reference), thus decreasing the chance that the oligonucleotide mismatch with the target nucleic acid will be repaired. Also preferred is E. coli DH5α.

The invention will better be understood by reference to the following examples, which is intended to merely illustrate the best mode now known for practicing the invention, but the invention is not to be considered limited thereto.

EXAMPLES

1. Site-directed Mutagenesis of Methionines 291 and 388 of Thrombomodulin

The 6 EGF-like domains region of native human thrombomodulin has two methionine residues, one at position 291 and one at position 388. (See FIG. 3). Oligonucleotide-directed in vitro mutagenesis was used to convert either or both of these methionines to other amino acids.

a. Plasmid pTHR14

Figure 2A:
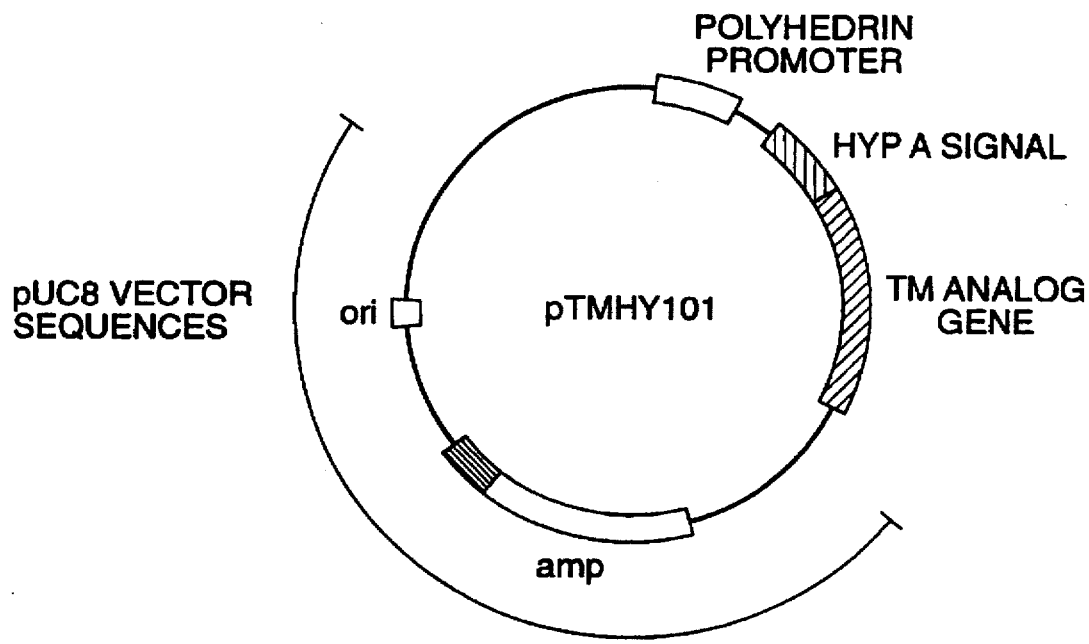
FIGS. 2A–2B depict baculovirus transfer vector pTMHY101 and a vector for making single-stranded DNA for use in site directed mutagenesis reactions, pTHR14.
Figure 2B:
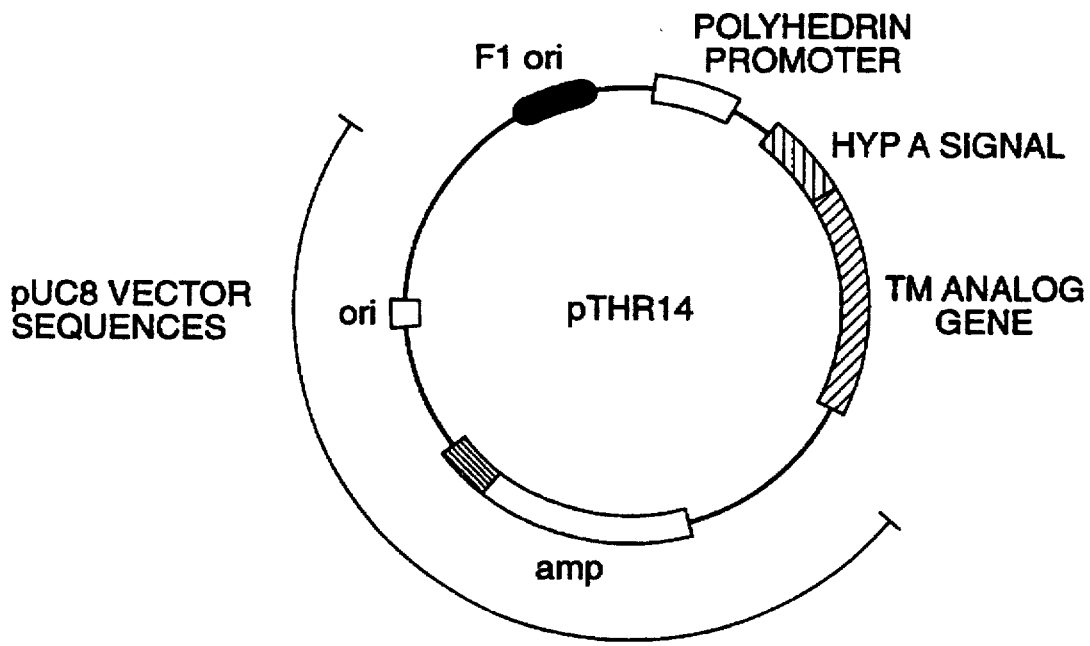
Figure 3C:
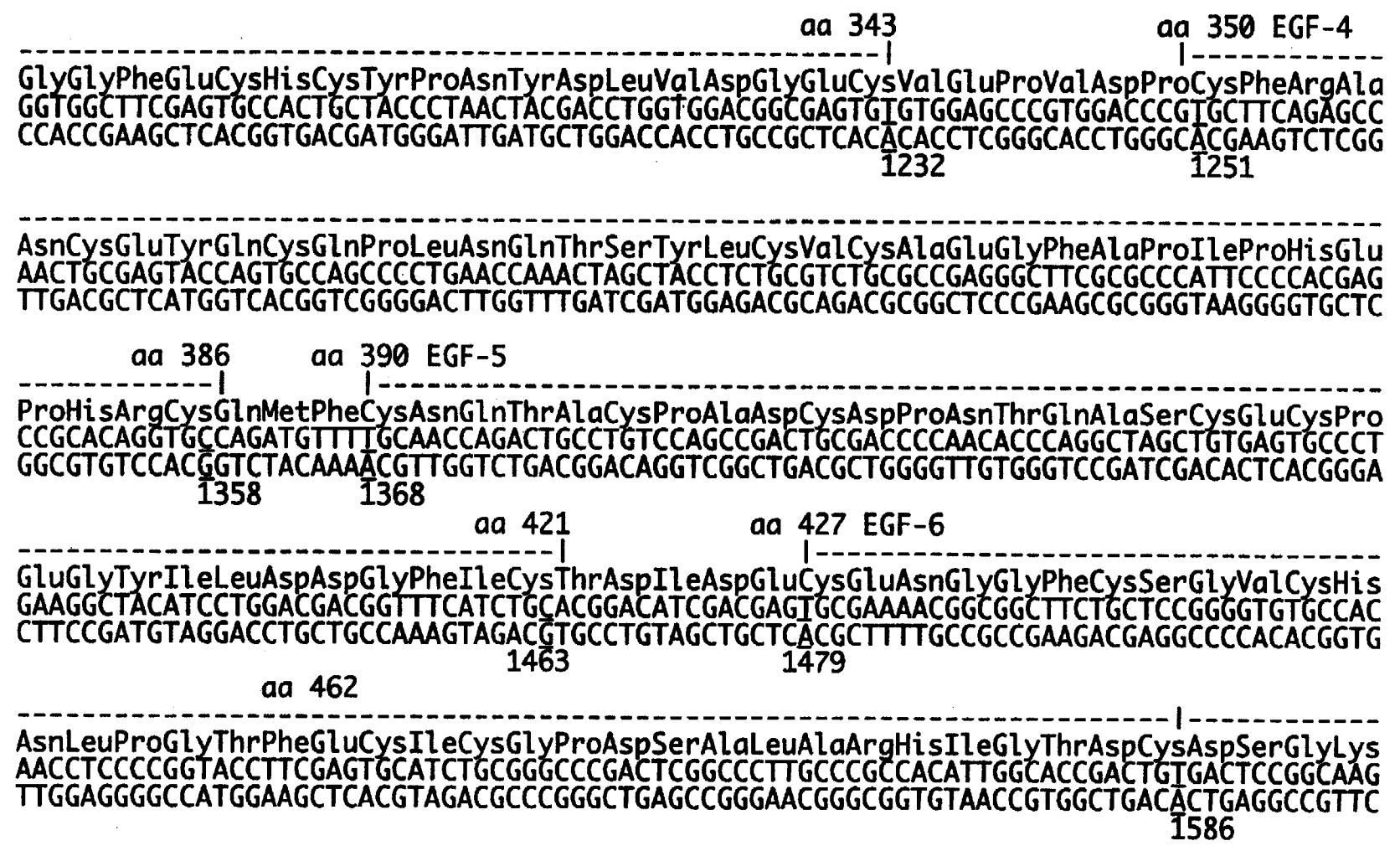

A plasmid for making single stranded DNA copies was constructed by ligating the F1 origin of replication contained on an AseI-ScaI fragment into an insect cell transfer vector, pTMHY101, previously digested with NdeI and ScaI. Plasmid pTMHY101 contains a gene sequence that produces a peptide corresponding to the 6 EGF-like domains of thrombomodulin, amino acids 227–462. The number 227–462 refer to the amino acids corresponding to the native thrombomodulin sequence (FIG. 3). Amino acids 227–462 comprise the 6 EGF-like domains. pTMHY101 is fully described in copending application U.S. Ser. No. 345,372 and is shown diagrammatically in FIG. 2.

b. Site-directed mutation

Specific mutagenizing oligonucleotide primers were synthesized and used with the MUTATOR™—DNA Polymerase III Site-directed Mutagenesis Kit (Catalogue #200500, Stratagene, La Jolla, Calif.), except as otherwise noted to prime second strand synthesis and create thrombomodulin analog genes with either one or both of the methionines changed to a non-oxidizable amino acid. Primers directing conversion to the preferred amino acids leucine, glutamine or alanine are shown in FIG. 4. Also included in these primers are substitutions in the nucleotide sequence that add a unique restriction enzyme site useful as a diagnostic for successful mutagenesis, but which do not necessarily change the corresponding amino acid sequence. The nucleotide substitutions are underlined in the primers shown in FIG. 4. For example, in plasmid pTHR28 the methionine at position 388 in the native thrombomodulin protein was replaced with leucine, and in the process a unique PvuII site was introduced. It is understood that other substituted non-oxidizable amino acids would be equally useful in this invention.

Purified single-stranded DNA templates were prepared using the procedure described by Bio-Rad (Muta-Gene Phagemid in vitro Mutagenesis, Instruction Manual, Cat. no. 170-3576, pgs. 33–34) although other procedures known in the art would be equally suitable.

The 5' terminus of each mutagenizing primer was phosphorylated by incubating 0.5 ng/ul of primer in a solution containing 2 mM rATP, 0.4 U/ul polynucleotide kinase in annealing buffer (20 mM Tris-HCl pH 7.5, 8 mM MgCl$_2$ and 40 mM NaCl) at 37° C. for 30 minutes. The reaction was heat inactivated by incubating the mixture at 65° C. for 15 minutes. The phosphorylated primer was annealed to the single-stranded template by heating 100 ng of template and 2.5 ng of primer in 25 ul of annealing buffer to 65° C. for 5 minutes, then allowing the mixture to cool and anneal at room temperature for 10 minutes. Double stranded DNA was made by primer extension essentially as described by Tsurushit, N., et al., (1988) Gene 62:135–139 and O'Donnell, M. E., et al., (1985) J. Biol. Chem. 260:12875–12883. Briefly, the template/primer mixture was diluted (1:1) with 10% annealing buffer plus 80 ug/ml bovine serum albumin, 2.5 mM dithiothreitol, 0.25 mM mixed dNTPs, 2 mM rATP and 1% glycerol plus 1 ug of single-stranded DNA binding protein. The reaction was incubated for 5 minutes at room temperature to allow the binding protein to coat the single-strand DNA template. DNA polymerase III holoenzyme (E. coli, 1.7 ul of 50 U solution) was added, and the reaction was incubated at 30° C. for 10 minutes. T4 DNA ligase was added (0.5 ul, 2 Weiss units) and the reaction was further incubated for 5 minutes at 30° C. This mixture was used to transform E. coli and properly mutated clones were selected by restriction digest pattern.

2. High Copy Mutagenesis Vectors for Site-Directed Mutagenesis

Several new high copy mutagenesis vectors useful for the mutagenesis methods of the present invention have been developed.

A series of plasmid vectors contain antibiotic resistance markers providing chloramphenicol resistance and an ampicillin resistance gene containing a mutation rendering it ampicillin sensitive. They contain f1 and ColEI origins of replication, and a polylinker inserted into the β-galactosidase gene. This series includes pBBS92, pBBS99, pBBS100, pBBS101, and pBBS122, all shown in FIG. 5, and pBBS89, shown in FIG. 6.

Figure 7A:
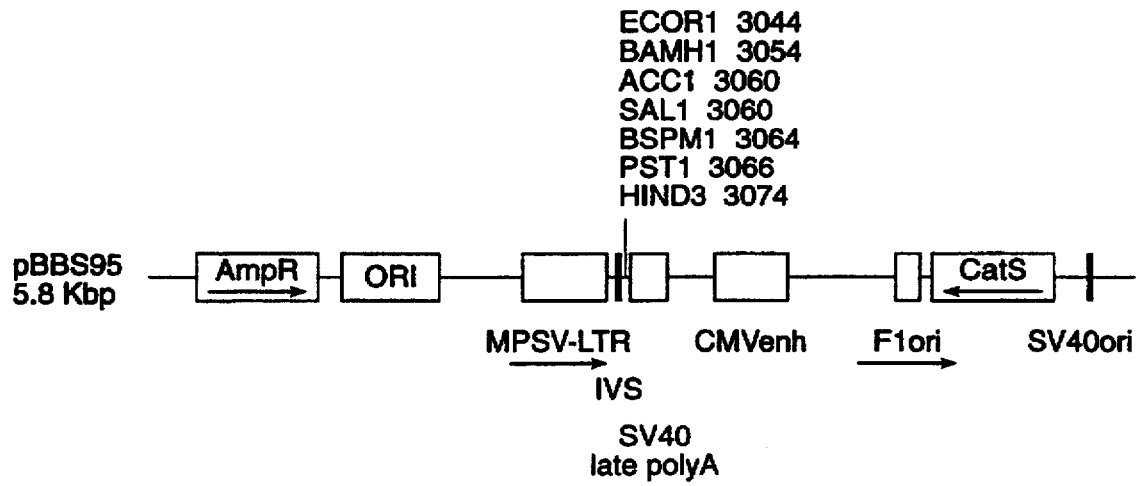
FIGS. 7A–7B are a schematic map of a portion of mutagenesis/selection vectors pBBS95 and 97, which are useful for the transient expression of cloned polypeptide-encoding target sequences in mammalian cells. Their features include: the ColE1 origin of replication ("ORI") and the phage f1 origin of replication ("F1ori") and two antibiotic resistance markers, an ampicillin resistance gene ("AmpR"), and an chloramphenicol acetyl transferase gene, which provides chloramphenicol resistance, but which is nonfunctional (i.e., sensitive) due to a mutation which may be easily repaired by site-directed mutagenesis ("CatS"). They also include EcoRI and HindIII cloning sites (pBBS97) or a polylinker (pBBS95) situated so as to allow transcription of cloned polypeptide-encoding target sequences driven by the MPSV promoter ("MPSV pro"); the SV40 late polyA addition sequence ("SV40 late polyA"), cytomegalovirus enhancer ("CMVenh"), and SV40 virus origin of replication ("SV40ori"). The vector pBBS97 also includes the puromycin-N-acetyl-transferase gene ("Pac"), which confers puromycin resistance. The orientation of transcription or replication is shown by an arrow. It should be noted that pBBS96 is identical to pBBS95, except that the SV40 ori sequence is in the opposite orientation; and pBBS98 is identical to pBBS97, except that the Pac gene and SV40 ori are in the opposite orientation.
Figure 7B:
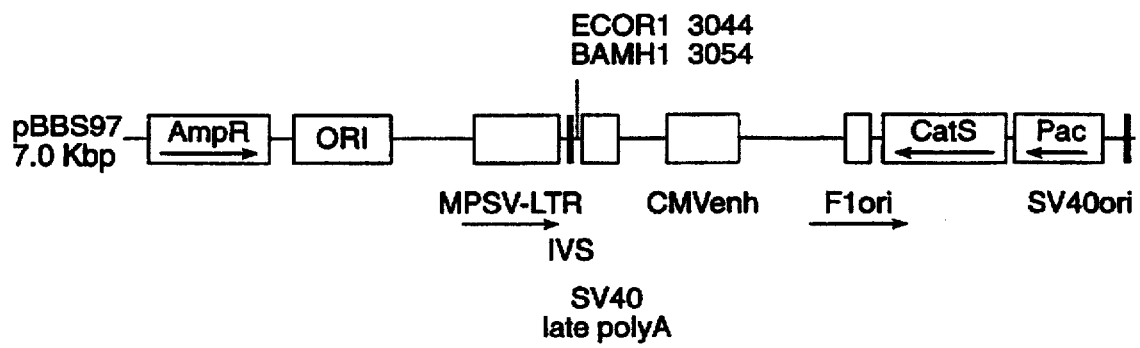
Figure 8:
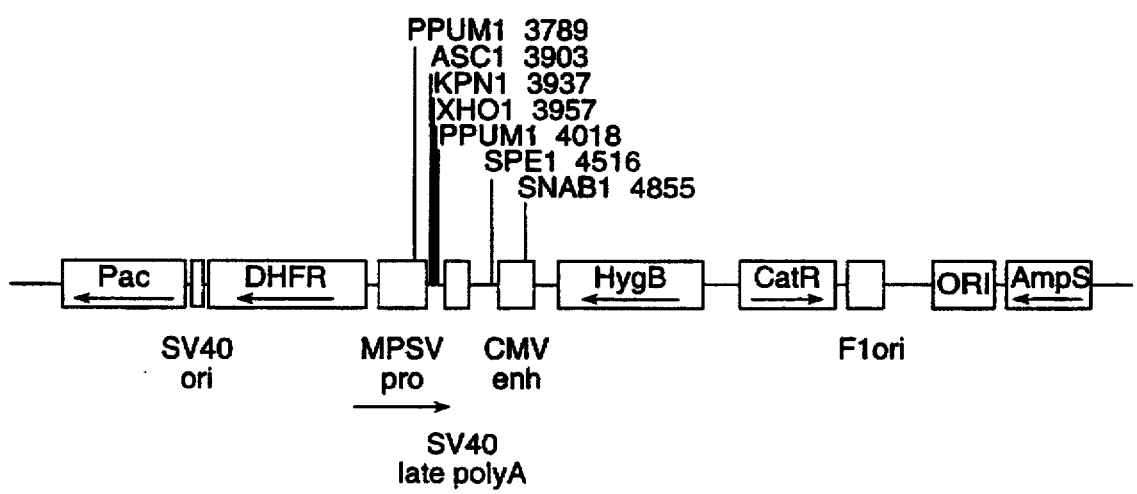
FIG. 8 is a schematic map of a portion of mutagenesis/selection vectors pBBS82 and 83, which are useful for expression of cloned polypeptide-encoding target sequences in mammalian cells. Their features include: the ColE1 origin of replication ("ORI") and the phage f1 origin of replication ("F1ori") and two antibiotic resistance markers, the chloramphenicol acetyl transferase gene, which provides resistance to chloramphenicol (CatR) and an ampicillin resistance gene which is nonfunctional (i.e., sensitive) due to a mutation which may be easily repaired by site-directed mutagenesis (AmpS). They also include a polylinker situated so as to allow transcription of cloned polypeptide-encoding target sequences driven by the MPSV promoter ("MPSV pro"); the SV40 late polyA addition sequence ("SV40 late polyA"), cytomegalovirus enhancer ("CMVenh"), and SV40 virus origin of replication ("SV40ori"). Also included are additional resistance markers for selection of mammalian cells containing the vectors: the puromycin-N-acetyl-transferase gene ("Pac"), which confers puromycin resistance, the hygromycin B resistance gene ("HygB"), and the amplifiable marker dihydrofolate reductase ("DHFR"), which confers methotrexate resistance. The orientation of transcription is shown by an arrow.
Figure 9:
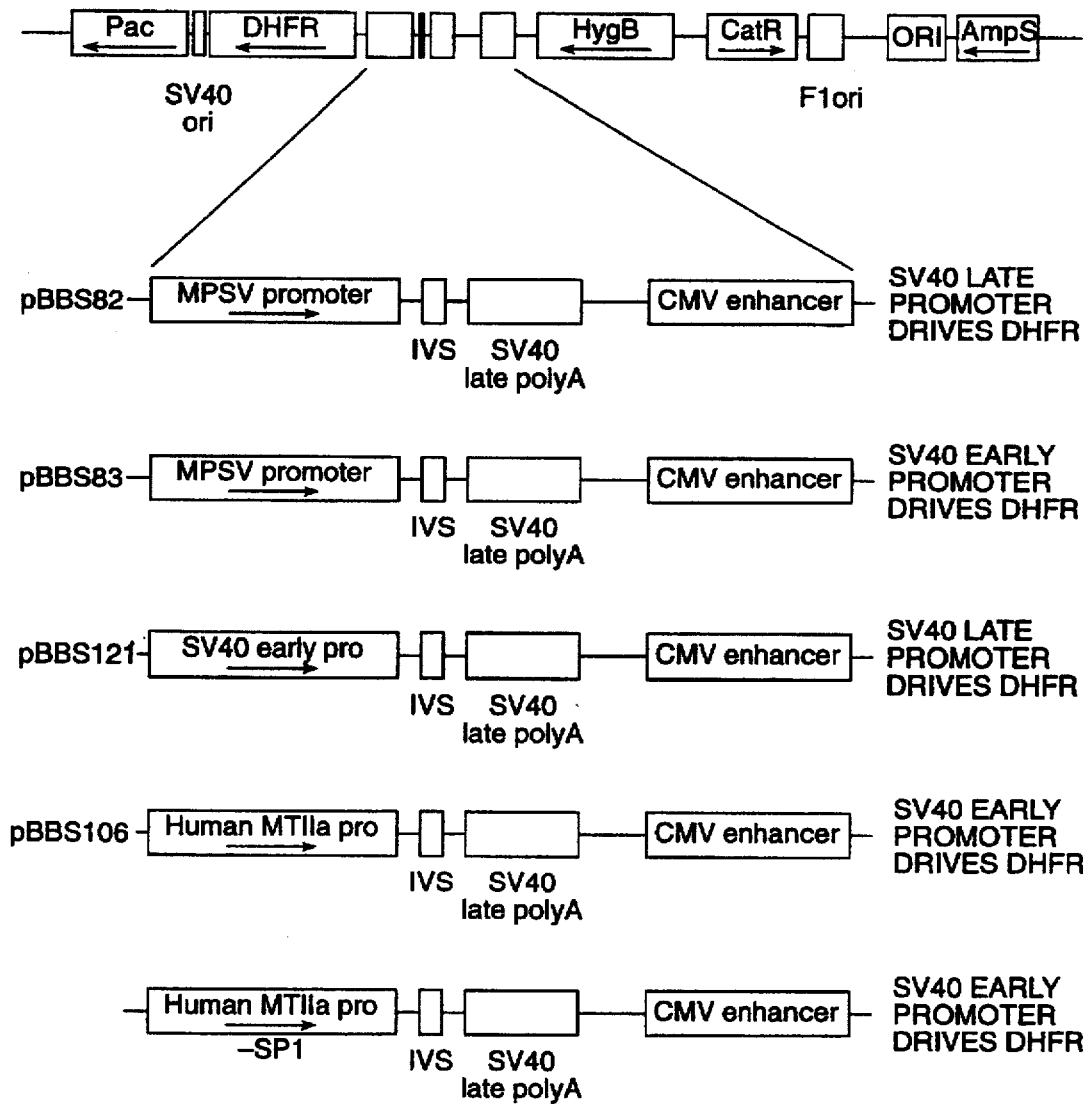
FIG. 9 is a schematic map of a portion of mutagenesis/selection vectors pBBS82, pBBS83, pBBS121, and pBBS106 which are useful for the stable expression of cloned polypeptide-encoding target sequences in mammalian cells. Their features include: the ColE1 origin of replication ("ORI") and the phage f1 origin of replication ("F1ori") and two antibiotic resistance markers, the chloramphenicol acetyl transferase gene, which provides resistance to chloramphenicol (CatR) and an ampicillin resistance gene which is nonfunctional (i.e., sensitive) due to a mutation which may be easily repaired by site-directed mutagenesis (AmpS). They also include cloning sites (not shown) situated between a mammalian promoter and intervening sequence (IVS) and the SV40 polyA addition sequence ("SV40 late polyA") so as to allow transcription of cloned polypeptide-encoding target sequences driven by the MPSV promoter ("MPSV pro") (pBBS82 and pBBS83), the SV40 early promoter ("SV40 Early Pro") (pBBS121), or the human metallothionein IIa promoter ("Human MTIIa Pro") (pBBS106). In addition, they also include the cytomegalovirus enhancer ("CMVenh"), and SV40 virus origin of replication ("SV40ori"). Also included are additional resistance markers for selection of mammalian cells containing the vectors: the puromycin-N-acetyl-transferase gene ("Pac"), which confers puromycin resistance, the hygromycin B resistance gene ("HygB"), and the amplifiable marker dihydrofolate reductase ("DHFR"), which confers methotrexate resistance, whose expression is driven by the SV40 late promoter (pBBS82 and pBBS121) or by the SV40 early promoter (pBBS83 and pBBS106). The orientation of transcription is shown by an arrow.

Eukaryotic expression/mutagenesis vectors are also provided. These likewise contain f1 and ColEI origins of replication, and ampicillin and chloramphenicol resistance markers for easy in vitro mutagenesis and selection in E. coli hosts. They also contain a polylinker situated so as to provide for the expression of cloned target sequences driven by various mammalian promoters, such as the MPSV (pBBS82, pBBS83), SV40 early (pBBS121), or human metallothionein IIa (pBBS106) promoters for the expression in mammalian cells of polypeptide-encoding target sequences cloned into the polylinker. All also contain the SV40 late polyA addition sequences and the cytomegalovirus (CMV) enhancers. These are shown in FIGS. 7–9. In vectors pBBS82 and pBBS121, DHFR expression is controlled by the weak SV40 late promoter to allow increased amplification in cell lines (e.g., CHODXB11) that lack an endogenous DHFR activity. DHFR expression is controlled by the strong SV40 early promoter in pBBS83 and pBBS106 to allow amplification in cell lines that do contain an endogenous DHFR activity.

Figure 10A:
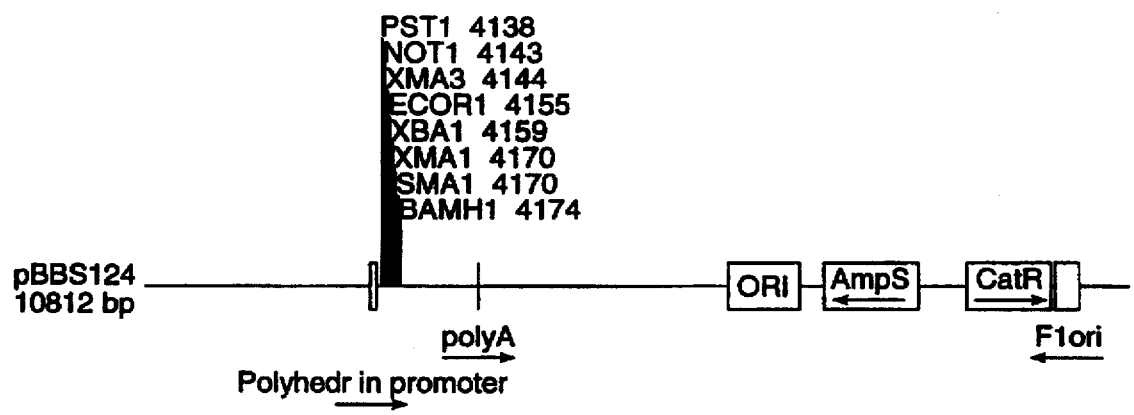
FIGS. 10A-10B are schematic maps of a portion of baculovirus mutagenesis/selection vectors pBBS124 and pBBS125 which are useful for the stable expression of cloned polypeptide-encoding target sequences in insect cells. Their features include: the ColE1 origin of replication ("ORI") and the phage f1 origin of replication ("F1ori") and two antibiotic resistance markers, the chloramphenicol acetyl transferase gene, which provides resistance to chloramphenicol ("CatR") and an ampicillin resistance gene which is nonfunctional (i.e., sensitive) due to a mutation which may be easily repaired by site-directed mutagenesis ("AmpS"). They also include a polylinker situated between the baculovirus polyhedrin promoter and a polyA addition sequence ("polyA") so as to allow transcription of cloned polypeptide-encoding target sequences. The direction of transcription, polyA addition (and of transcription of cloned target sequences) and of replication are shown by arrows.
Figure 10B:
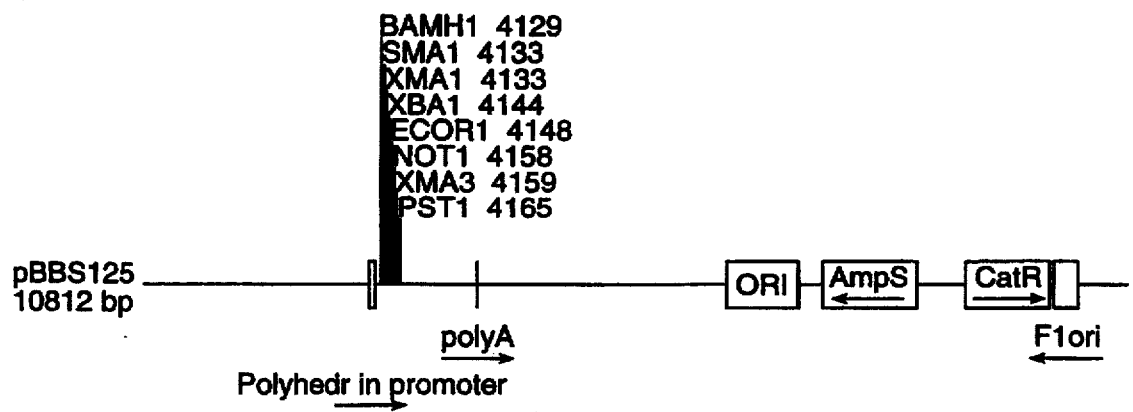
Figure 11A:
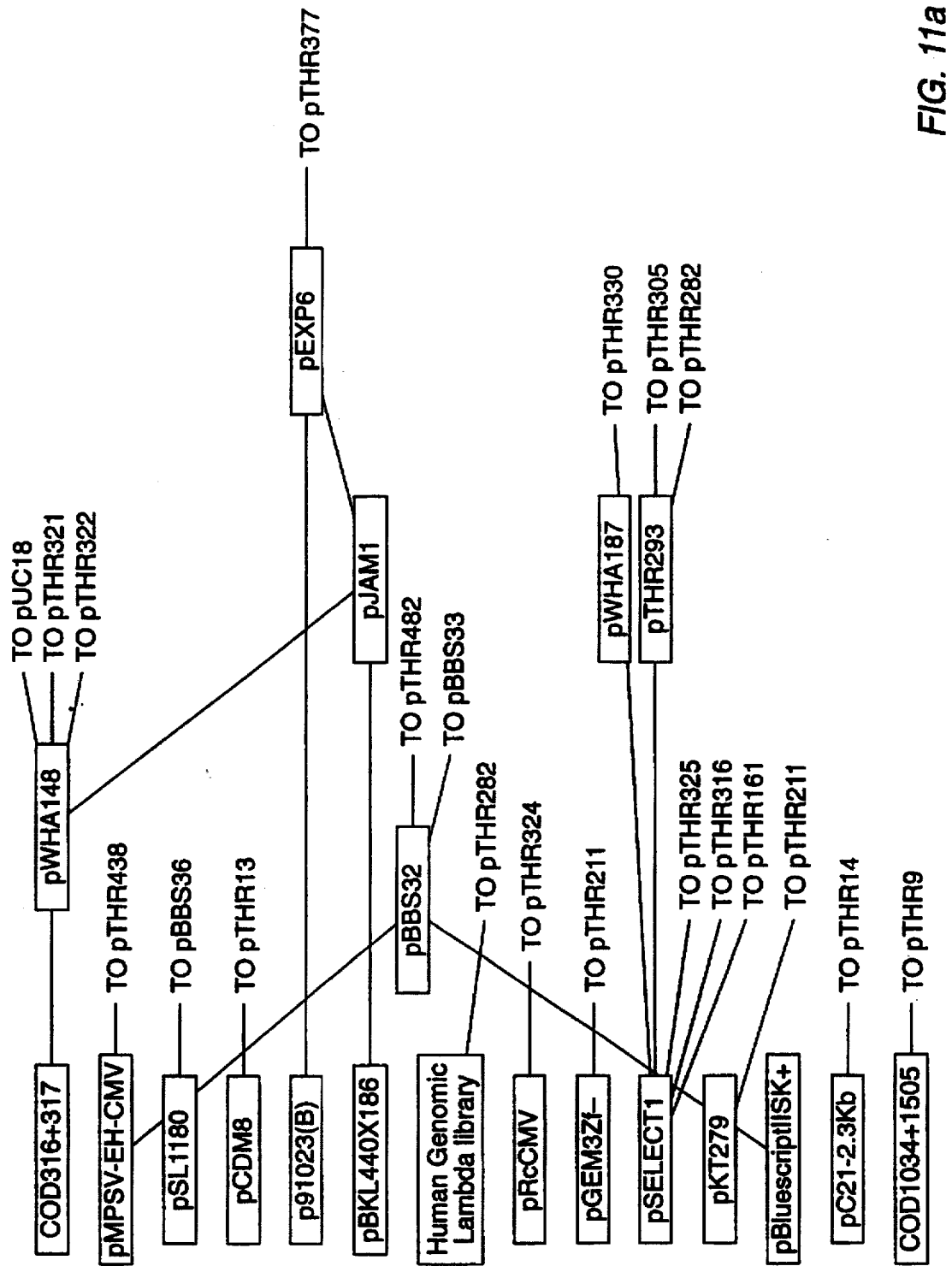
FIGS. 11 and 12 diagram the manner in which the mutagenesis/selection vectors shown in FIGS. 5 through 10 were derived.
Figure 11B:
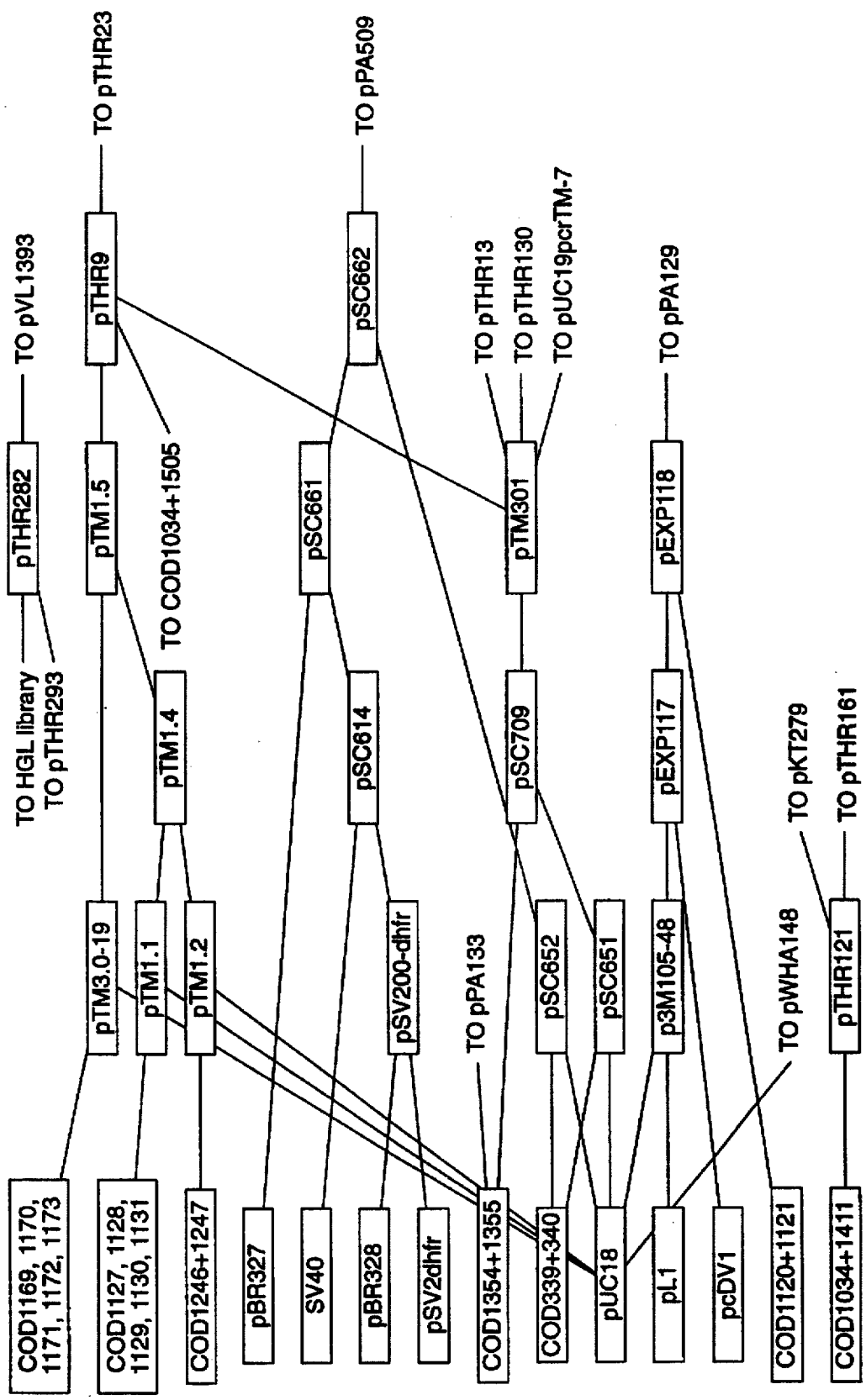
Figure 11C:
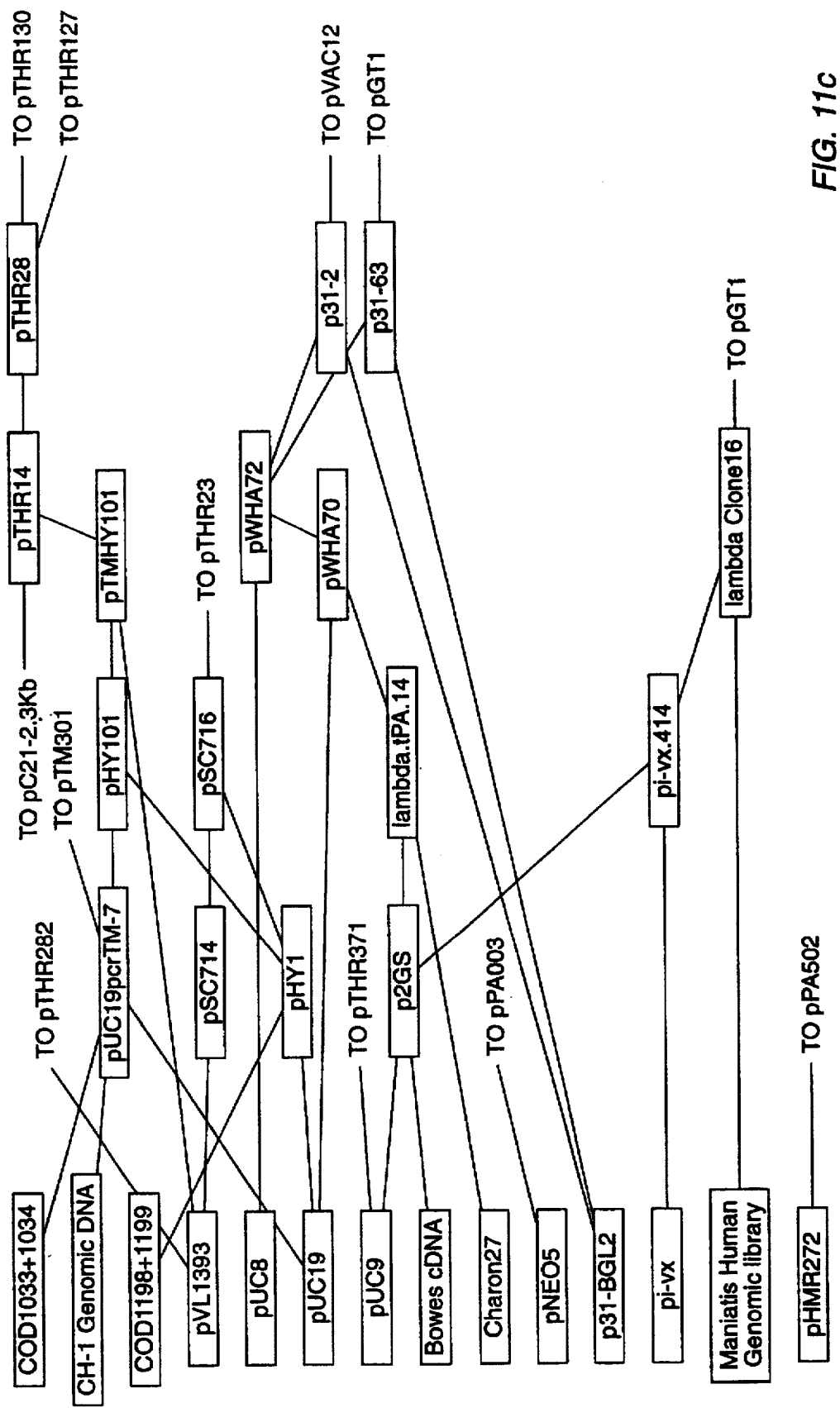
Figure 11D:
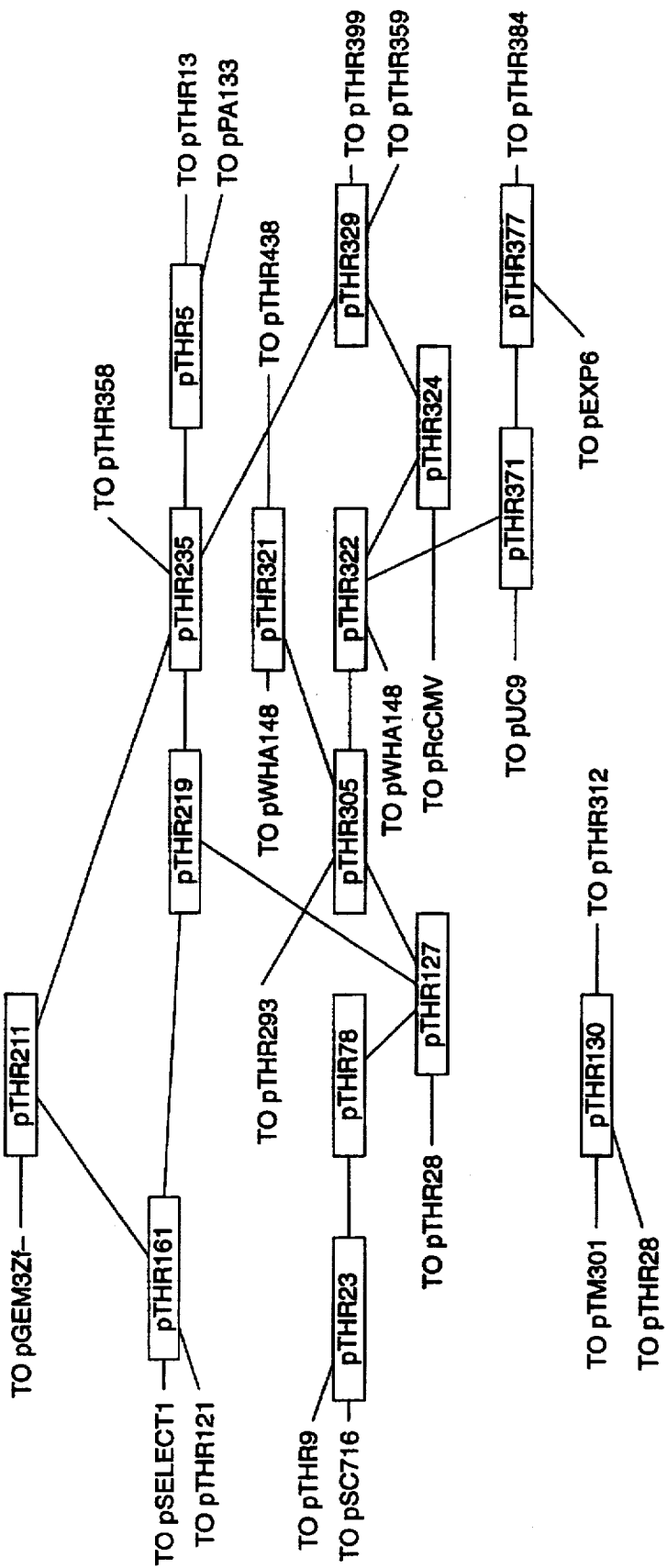
Figure 11E:
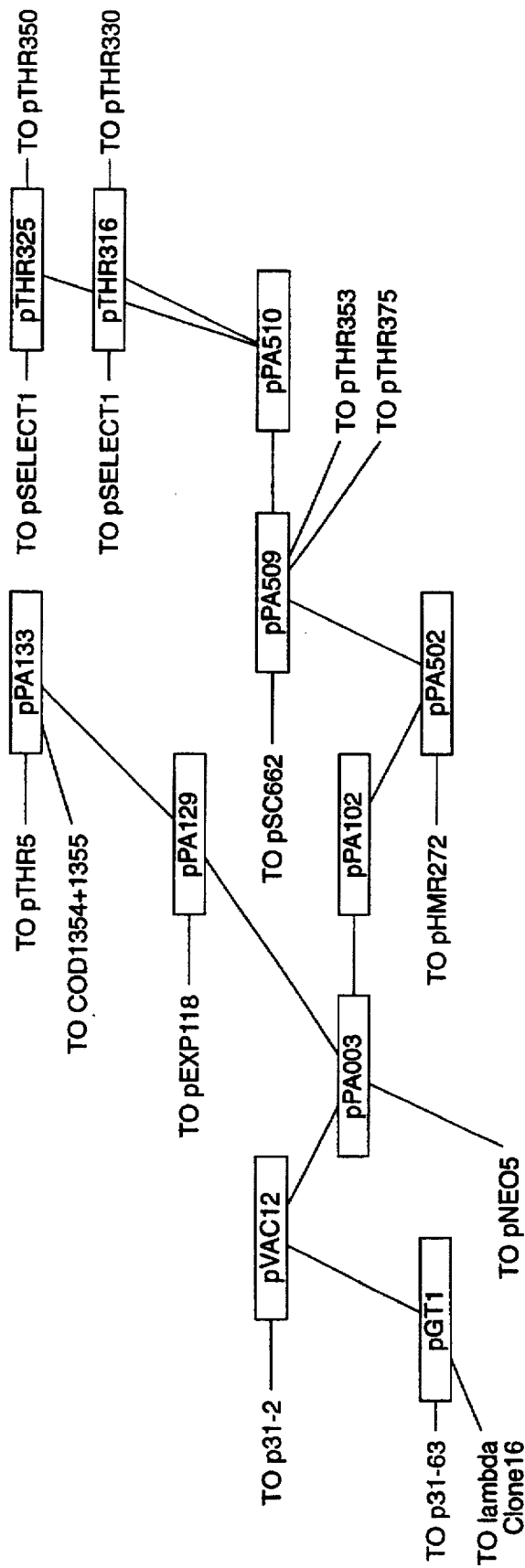
Figure 11F:
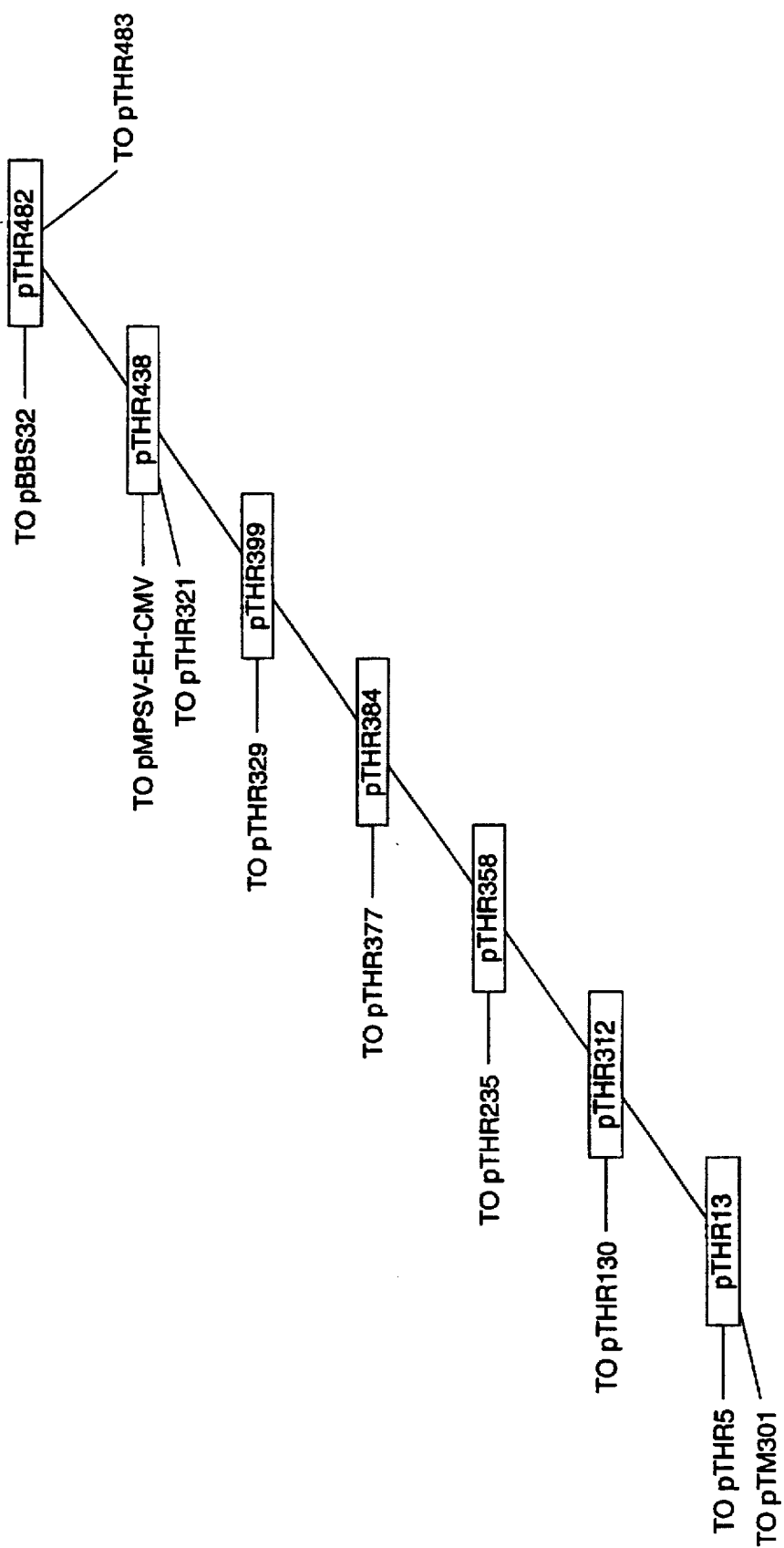
Figure 11G:
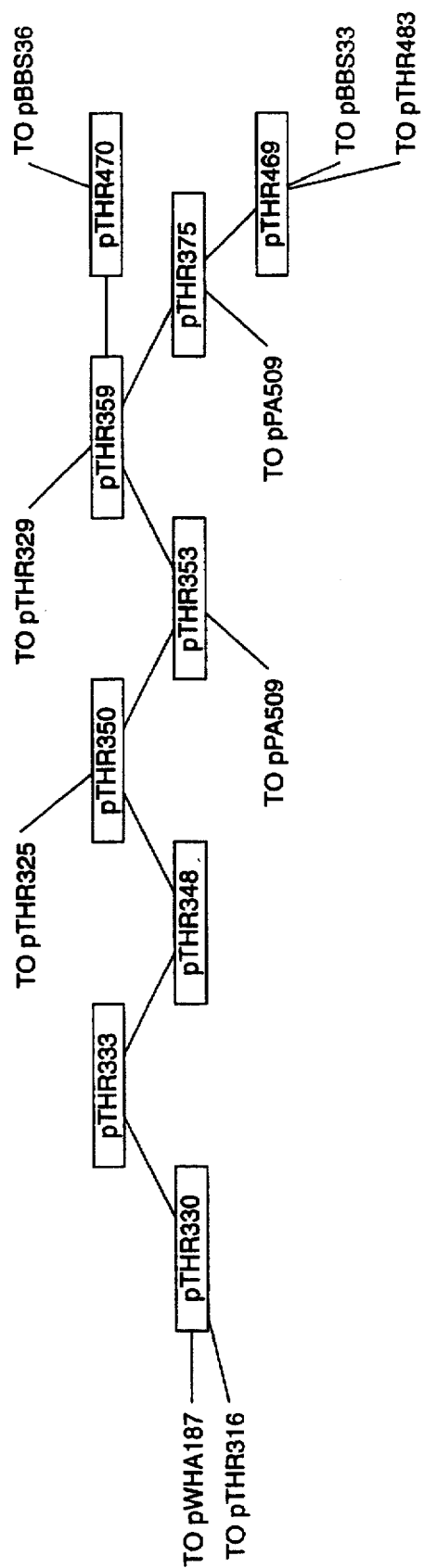
Figure 11H:
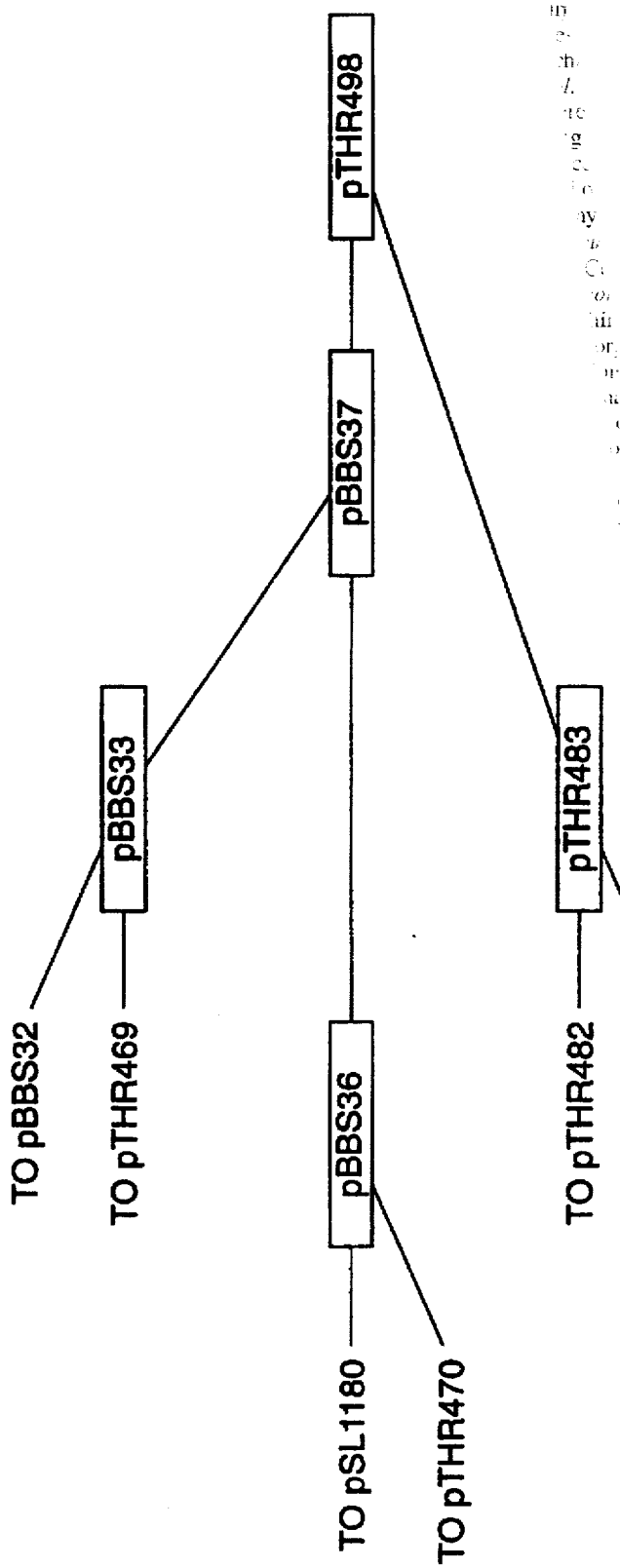

Baculovirus mutagenesis/expression vectors pBBS124 and pBBS125 are also provided (FIG. 10). In these vectors, which likewise contain ColEI and f1 origins of replication and ampicillin and chloramphenicol resistance markers, a polylinker situated so as to provide for the expression of cloned target sequences driven by the polyhedrin promoter.

Figure 5:
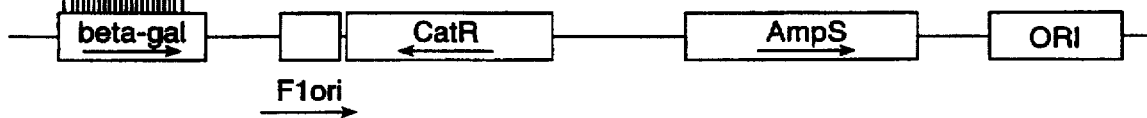
FIG. 5 (SEQ ID NOS: 46, 42, 31, and 41) is a schematic map (not to scale) of the region of cloning/mutagenesis vector pBBS104 which includes: a polylinker which interrupts the β-galactosidase gene ("beta-gal"), the ColE1 origin of replication ("ORI") and the phage f1 origin of replication ("F1ori") and two antibiotic resistance markers, the chloramphenicol acetyl transferase gene, which provides resistance to chloramphenicol (CatR) and an ampicillin resistance gene which is nonfunctional (i.e., sensitive) due to a mutation which may be easily repaired by site-directed mutagenesis (AmpS). The orientation of transcription or replication is shown by an arrow. These features are shared with the related vectors pBBS92, pBBS99, pBBS100, pBBS101 and pBBS122.
Figure 6:
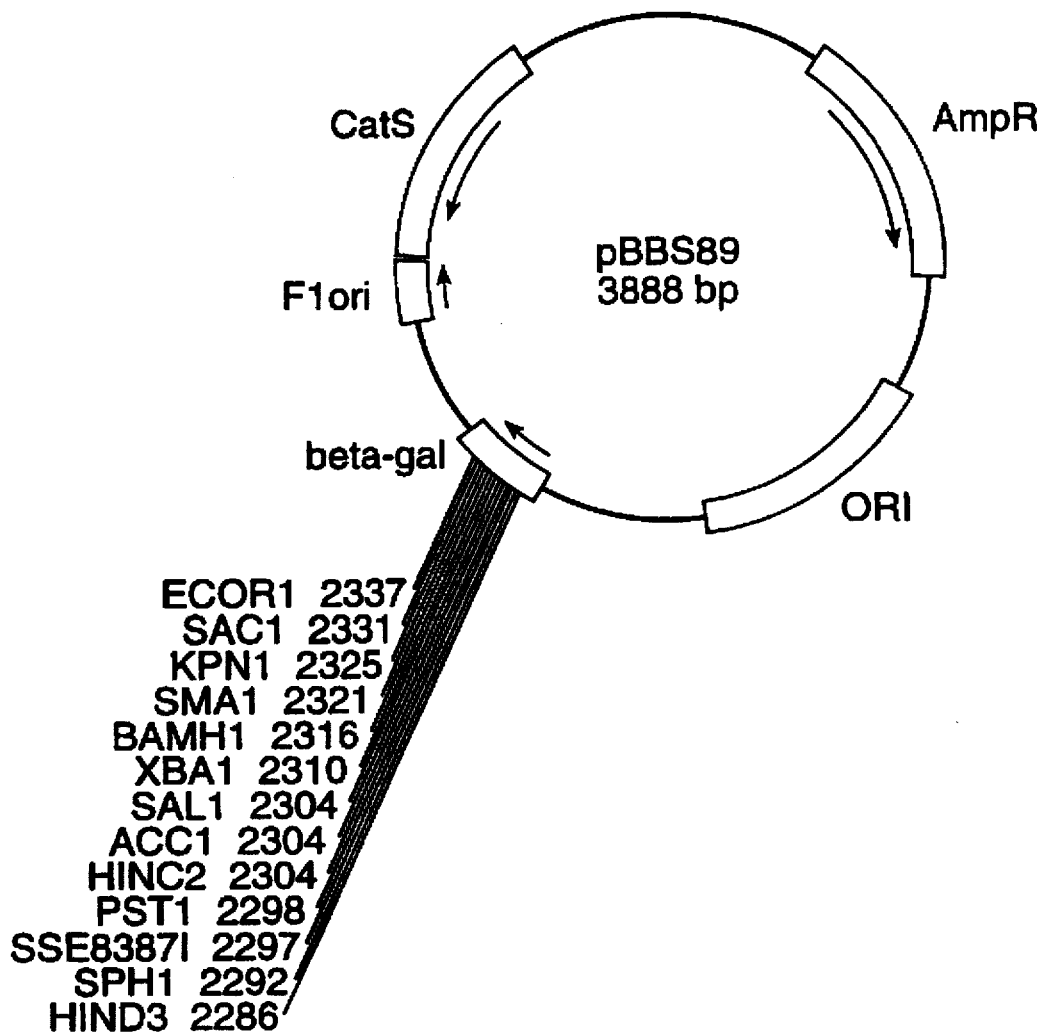
FIG. 6 is a schematic map of mutagenesis/selection vector pBBS89. Its features include: a polylinker which interrupts the β-galactosidase gene ("beta-gal"), the ColE1 origin of replication ("ORI") and the phage f1 origin of replication ("F1ori") and two antibiotic resistance markers, an ampicillin resistance gene (AmpR), and an chloramphenicol acetyl transferase gene, which provides chloramphenicol resistance, but which is nonfunctional (i.e., sensitive) due to a mutation which may be easily repaired by site-directed mutagenesis (CatS). The orientation of transcription or replication is shown by an arrow.

Oligonucleotides which may be used for changing the ampicillin and chloramphenicol resistance genes from sensitivity to resistance or vice versa in any of the vectors shown in FIGS. 5–10 are shown in FIG. 5.

Figure 12A:
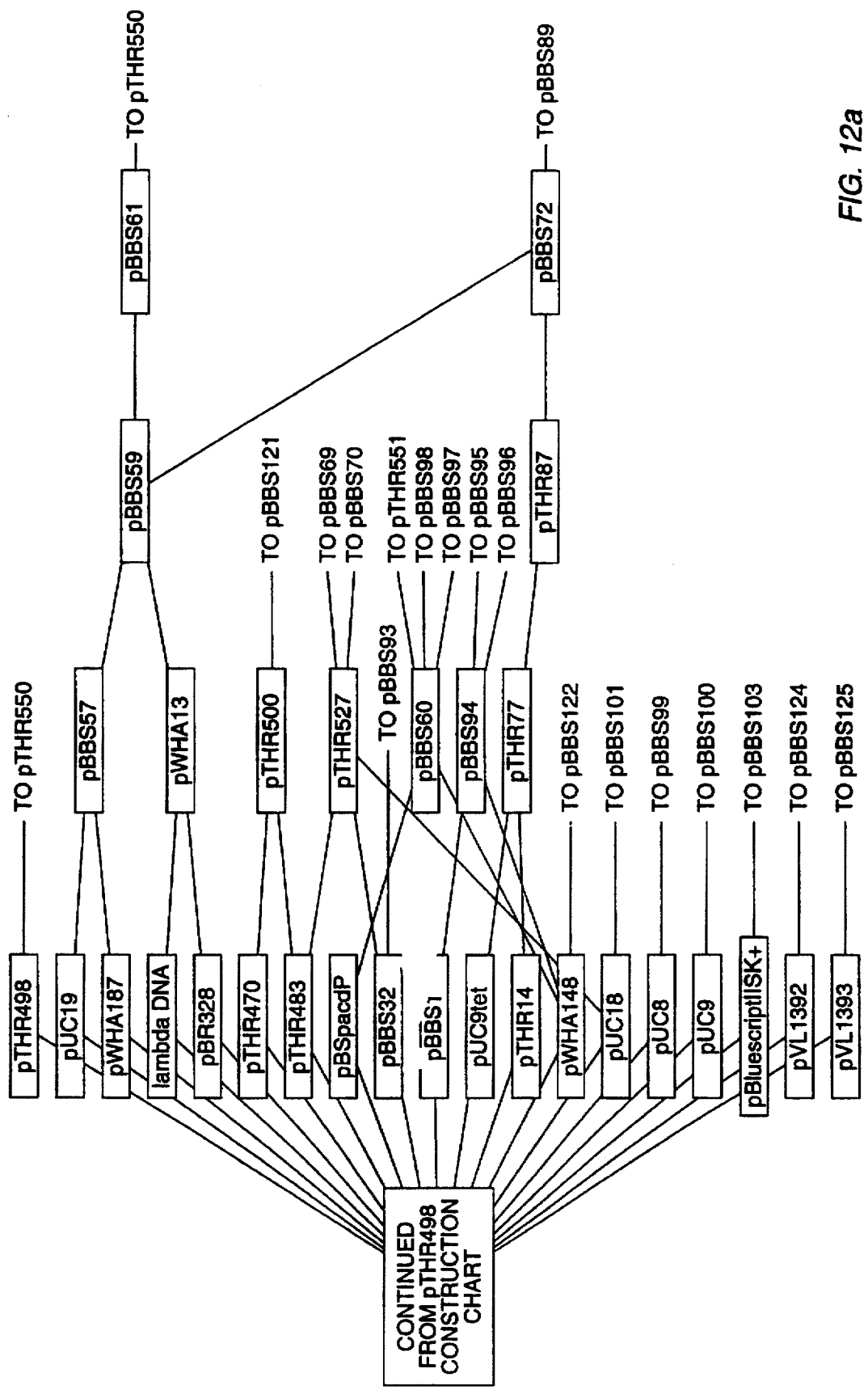
Figure 12B:
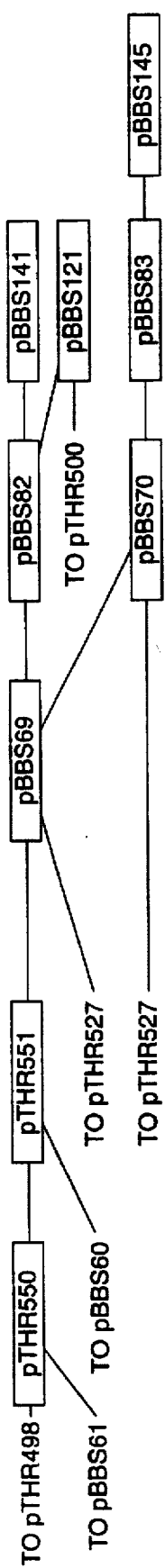
Figure 12C:
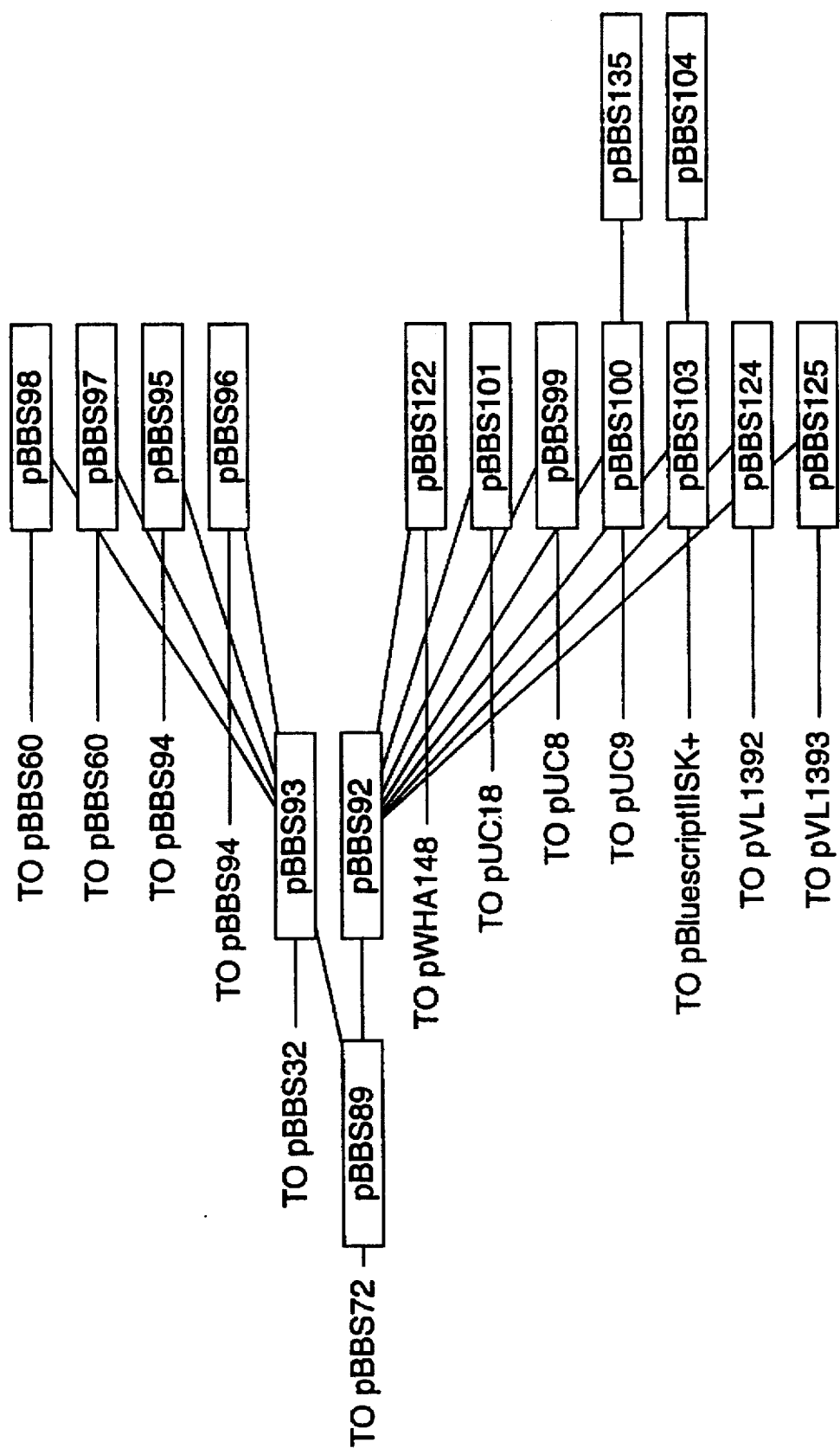

Details on the construction of the mutagenesis vectors shown in FIGS. 5–10 are given below, along with a description of the plasmids, phage, libraries, etc., which were employed in their construction. A schematic for the construction of the mutagenesis vectors is given in FIGS. 12 and 13. Additional information regarding their construction is given in the following U.S. patents or co-pending U.S. patent applications, which are hereby incorporated by reference:

U.S. Pat. Nos.
4,870,006
4,960,702
5,017,478
5,043,341
5,082,775.

U.S. Patent Applications
U.S. Ser. No. 789,787, filed Nov. 8, 1991, now abandoned
U.S. Ser. No. 700,028, filed May 14, 1991, now abandoned
U.S. Ser. No. 859,633, filed Mar. 20, 1992, now abandoned
U.S. Ser. No. 345,372, filed Apr. 28, 1989, now abandoned
U.S. Ser. No. 730,975, filed Jul. 29, 1991, now abandoned
U.S. Ser. No. 406,941, filed Sep. 13, 1989, now abandoned
U.S. Ser. No. 506,325, filed Apr. 9, 1990, now U.S. Pat. No. 5,256,770
U.S. Ser. No. 568,456, filed Aug. 15, 1990, now abandoned
U.S. Ser. No. 724,237, filed Jul. 1, 1991, now abandoned It will be readily apparent to those skilled in the art that it is possible to construct these or functionally identical or similar vectors in a number of ways, employing origins of replication, marker sequences, polyA addition sequences, enhancers, polylinkers or other features which are widely and readily available, whether from published sequences, from commercial vendors, or from other sources.

Description of Plasmids and Phage Used in the Construction of Mutagenesis Plasmids Note: All COD designations refer to oligonucleotides listed below.

All plasmids, libraries and phage or viral DNA listed below and not otherwise described are well known in the art and widely available, e.g., from vendors such as Pharmacia, Stratagene, New England Biolabs, etc. The indicated plasmids were deposited with the American Type Culture Collection, Rockville, Md. on Jul. 22, 1997.

lambda.clone16. From the Maniatis human genome library containing the genomic signal sequence of tissue plasminogen activator (tPA) isolated by recombination with πvx.414.

lambda.tpa.14. BglII fragment from cDNA made from Bowes melanoma cell line (CHL-1) containing the coding sequence for mature tPA inserted into the BamHI site of lambda phage Charon 27.

p2G5. PstI fragment from cDNA made from Bowes melanoma cell line (CHL-1) containing the coding sequence for amino acids 7–145 of mature tPA inserted into the PstI site of pUC9. The coding sequence of tPA is oriented in the same direction as the Lac promoter.

p31-2. XhoII fragment of pWHA72 containing the coding sequence for mature tPA inserted into the BglII site of p31-BglII. The coding sequence of tPA is oriented so that the NarI site in the coding sequence is about 2300 bp from the BamHI site in the vector.

p31-63. XhoII fragment from pWHA72 containing the coding sequence for mature tPA inserted into the BamHI-BglII sites of p31-BglII. The coding sequence of tPA is oriented so that the resulting unique BglII site is at the N-terminus of mature tPA.

p3M105-48. HindIII-PstI fragment from pL1 (Pharmacia) containing the SV40 promoter inserted into the HindIII-PstI asites of pUC18.

pBBS1. pCD2 modified as described in Nature 342:684. Modification is the addition of the polylinker (SEQ ID NO:52) 5'-tgcagtctagacccgggaattcgggcccggatc-3' into the PstI-BamHI sites of pCD2 (See Mol. Cell. Biol. 7:2745).

pBBS32. BglII-ApaI fragment from polymerase chain reaction (PCR) of pMPSV-EH-CMV using COD2168 and COD2169 and containing the MPSV promoter through the CMV enhancer inserted into the BamHI-ApaI sites of pBluescriptIISK+ (Stratagene). This creates a MPSV-polylinker-SV40 polyA-CMV enhancer cassette in pBluescript.

pBBS33. SspI-RsrII fragment from pBBS32 containing MPSV-EH-CMV inserted into the PvuII-PpumI sites of pTHR469. This creates a plasmid containing the MPSV promoter, SV40polyA, and CMV enhancer that can be used as a vector for stable clones.

pBBS36. AflII-NcoI fragment from pTHR470 containing the SV40 origin of replication (ori), enhancer and SV40 late promoter, inserted into the AflII-NcoI sites of pSL1180.

pBBS37. MscI-BstXI fragment from pBBS36 containing the SV40 late promoter inserted into the PvuII-BstXI sites of pBBS33 to make a mammalian expression vector that uses the MPSV promoter and CMV enhancer and which has the DHFR expression drived by the SV40 late promoter. This plasmid also contains the hygromycin B gene.

pBBS57. ScaI-EcoRI fragment from pWHA187 containing the f1 ori inserted into the ScaI-EcoRI sites of pUC19.

pBBS59. BsaAI-ScaI fragment of pWHA13 containing most of the chloramphenicol acetyl transferase (CAT) gene inserted into the SnaBI site of pBBS57. The CAT gene is oriented in the opposite direction as the ampicillin resistance (Amp) gene. Note: this is the opposite orientation of pBBS58 and pBBS58 has a 2-3-fold lower copy number.

pBBS60. PvuII-BamHI fragment of pBSpacdp containing the puromycin resistance gene inserted into the StuI-BamHI sites of pWHA148.

pBBS61. PvuII(partial)-FspI(partial) deletion of pBBS59 to delete the β-galactosidase promoter and alpha complementing coding sequence. This leaves a plasmid that contains the f1 ori, CAT gene, Amp gene, and ColEI ori.

pBBS69. KpnI-SpeI fragment of pBBS32 containing the MPSV promoter inserted into the KpnI-SpeI sites of pTHR551 to make a mammalian expression vector that uses the MPSV promoter, has three selectable markers (PAC, DHFR, and HygB), has the SV40 late promoter expressing the DHFR gene, has the SV40 ori, the CAT and Amp genes, and the f1 ori. Note: an ApaI site restriction maps near the unique XcmI site.

pBBS70. BstXI-KpnI fragment from pTHR527 containing the SV40 early promoter and N-terminus of the DHFR gene inserted into the BstXI-KpnI sites of pBBS69 to make a mammalian expression vector that uses the MPSV promoter, has three selectable markers (PAC, DHFR, HygB), has the SV40 early promoter driving expression of the DHFR gene, has two SV40 ori's, contains the CAT and Amp genes, and contains the f1 ori. Note: an ApaI site restriction maps near the unique XcmI site.

pBBS72. AatII-AlwNI fragment of pTHR87 containing the Amp$^r$ gene inserted into the AatII-AlwNI sites of pBBS59 to make a new "high copy number" mutagenesis vector that contains the Amp$^s$ and CAT genes.

pBBS82 (ATCC Accession No. 209158). COD 1632 was used in in vitro mutagenesis to convert Amp$^r$ to Amp$^s$ in pBBS69, also creating an XcmI site. This plasmid is now a mammalian mutagenesis/expression vector that uses the MPSV promoter, has three selectable markers (PAC, DHFR, HygB), the SV40 late promoter driving expression of the DHFR gene, and an SV40 ori, and contains the CAT and Amp$^s$ genes and the f1 ori. Note: an ApaI site restriction maps near the unique XcmI site.

pBBS83 (ATCC Accession No. 209159). COD 1632 was used in vitro mutagenesis to convert Amp$^r$ to Amp$^s$ in pBBS70, also creating an XcmI site. This plasmid is now a mammalian mutagenesis/expression vector that uses the MPSV promoter, has three selectable markers (PAC, DHFR, HygB), the SV40 late promoter driving expression of the DHFR gene, and an SV40 ori, and contains the CAT and Amp$^s$ genes and the f1 ori. Note: an ApaI site restriction maps near the unique XcmI site.

pBBS89. COD1941 was used to destroy the EcoRI site in the CAT gene and to convert chloramphenicol resistance to sensitivity (i.e., Cm$^r$ to Cm$^s$) by in vitro mutagenesis of pBBS72. This also created an FspI site.

pBBS92 (ATCC Accession No. 209160). COD1940 was used to convert Cm$^s$ to Cm$^r$ by in vitro mutagenesis of pBBS89. This created an AvaI site. Also, COD1632 was used to convert Amp$^r$ to Amp$^s$. This created an XcmI site.

pBBS93. PvuI fragment from pBBS32 containing the MPSV promoter and CMV enhancer was inserted into the PvuI site of pBBS89 to make a mammalian expression/mutagenesis plasmid.

pBBS94. SphI-XhoI fragment of pBBS1 containing the SV40 ori was inserted into the SphI-SalI sites of pWHA148.

pBBS95 (ATCC Accession No. 209161). BamHI-BglII fragment of pBBS94 containing the SV40 ori was inserted into the BglII site of pBBS93. The fragment is oriented so that when digested with BssHII one obtains fragments of 2444, 1615, 1103, 578, and 51 bp. This is the opposite orientation of pBBS96. This plasmid is a mammalian expression/mutagenesis vector that contains the MPSV promoter, CMV enhancer, SV40 ori, Cm$^s$ and Amp$^s$ genes, and an f1 ori.

pBBS96 (ATCC Accession No. 209162). BamHI-BglII fragment from pBBS94 containing the SV40 ori inserted into the BglII site of pBBS93. The fragment is oriented so that when digested with BssHII, one obtains fragments of 2675, 1384, 1103, 578 and 51 bp. This is the opposite orientation of pBBS95.

pBBS97 (ATCC Accession No. 209163). BamHI-BglII fragment of pBBS60 containing the PAC gene inserted into the BglII site of pBBS93. The fragment is oriented so that the PAC gene is in the opposite orientation as the MPSV-LTR. This is the opposite orientation of pBBS98. This plasmis is a mammalian expression/mutagenesis vector that contains the MPSV promoter, CMV enhancer, PAC gene, SV40 ori, Cm$^s$ and Amp$^r$ genes, and f1 ori.

pBBS98 (ATCC Accession No. 209164). BamHI-BglII fragment of pBBS60 containing the PAC gene inserted into the BglII site of pBBS93. The fragment is oriented so that the PAC gene is in the same orientation as the MPSV-LTR. This is the opposite orientation as pBBS97.

pBBS99 (ATCC Accession No. 209165). FspI fragment from pBBS92 containing the Cat$^r$ gene, f1 ori, and part of the Amp$^s$ gene inserted into the FspI site of pUC8 to make a new mutagenesis vector containing the Cat$^r$ gene, f1 ori, Amp$^s$ gene, and the alpha complementing group of β-galactosidase from pUC8 including the pUC8 polylinker. This plasmid should substitute for pUC8.

pBBS100 (ATCC Accession No. 209166). FspI fragment from pBBS92 containing the Cat$^r$ gene, f1 ori, and part of the Amp$^s$ gene inserted into the FspI site of pUC9 to make a new mutagenesis vector containing the Cat$^r$ gene, f1 ori, Amp$^s$ gene and the alpha complementing group of β-galactosidase from pUC9 including the pUC9 polylinker. The plasmid should substitute for pUC9.

pBBS101 (ATCC Accession No. 209167). FspI fragment of pBBS92 containing the Cat$^r$ gene, f1 ori, and part of the Amp$^s$ gene inserted into the FspI site of pUC18 to make a new mutagenesis vector containing the Cat$^r$ gene, f1 ori, Amps gene and the alpha complementing group of β-galactosidase from pUC18, including the pUC18 polylinker. This plasmid should substitute for pUC18. Note: No substitute for pUC19 was made because pBBS92 is already a substitute for pUC19.

pBBS103. FspI fragment from pBBS92 containing the Cat$^r$ gene, f1 ori, and part of the Amp$^s$ gene inserted into the FspI site of pBluescriptIISK+ (Stratagens) to make a new mutagenesis vector containing the Cat$^r$ gene, f1 ori, Amp$^s$ gene and the alpha complementing group of β-galactosidase from pBluescriptIISK+, including the pBluescriptIISK+ polylinker. This plasmid could substitute for pBluescriptIISK+.

pBBS104 (ATCC Accession No. 209168). PmlI-SnaBI deletion of pBBS103 to delete XhoI site that is outside the polylinker.

pBBS121 (ATCC Accession No. 209169). BstXI-XhoI fragment from pTHR500 containing the SV40 early promoter inserted into the BstXI-XhoI sites of pBBS82.

pBBS122 (ATCC Accession No. 209170). BglI fragment from pBBS92 containing the Cm$^r$ gene, f1 ori, and part of the Amp$^s$ gene inserted into the BglI site of pWHA148 to make a new mutagenesis vector containing the Cm$^r$ gene, f1 ori, Amp$^s$ gene and the alpha complementing group of β-galactosidase from pWHA148, including the pWHA148 polylinker.

pBBS124 (ATCC Accession No. 209171). BglI fragment from pBBS92 containing the Amp$^s$ gene, the Cm$^r$ gene and the f1 ori inserted into the BglI site of pVL1392. This creates a baculovirus mutagenesis vector.

pBBS125 (ATCC Accession No. 209172). BglI fragment from pBBS92 containing the Amp$^s$ ene, the Cm$^r$ gene and the f1 ori inserted into the BglI site of pVL1393 to create a baculovirus mutagenesis vector.

pBBS135 (ATCC Accession No. 209173). COD2588 was used in in vitro mutagenesis to create a one base insertion in the polylinker of pBBS100, resulting in a different reading frame. Also, COD1941 was used to convert Cm$^r$ to Cm$^s$. This created a BspHI site. Also, COD1633 was used to convert Amp$^s$ to Amp$^r$. This created a FspI site.

pBBS141 (ATCC Accession No. 209174). COD2606 was used to delete the polylinker between the Amp gene and the PAC gene by in vitro mutagenesis of pBBS82. this destroyed an EcoRI site. Also, COD2607 was used to delete the first polylinker. This destroyed a HindIII site and a PstI site. Also, COD2609 was used to destroy the SalI site in the PAC gene.

Also, COD2610 was used to destroy the HindIII site upstream of the DHFR gene. Also, COD1941 was used to convert Cm$^r$ to Cm$^s$. This created a BspHI site. Also, COD2461 was used to convert Amp$^s$ to Amp$^r$. This created a FspI site.

pBBS145 (ATCC Accession No. 209175). COD2606 was used to delete the polylinker between the Amp gene and the PAC gene by in vitro mutagenesis of pBBS82. this destroyed an EcoRI site. Also, COD2607 was used to delete the first polylinker. This destroyed a HindIII site and a PstI site. Also, COD2609 was used to destroy the SalI site in the PAC gene. Also, COD2610 was used to destroy the HindIII site upstream of the DHFR gene. Also, COD1941 was used to convert Cm$^r$ to Cm$^s$. This created a BspHI site. Also, COD2461 was used to convert Amp$^s$ to Amp$^r$. This created a FspI site.

pBSpacdp. This plasmid contains the puromycin resistance gene and is described in Gene 62:121–126.

pEXP6. The XhoI-SalI fragment from pJAM1 containing the BKV enhancer in the "Late" orientation was inserted into the XhoI site of p91023(B) so that the "Late" sequence is in the same orientation as the Major Late Promoter of Adenovirus2.

pEXP117. HindIII-KpnI fragment from p3M105-48 containing the SV40 promoter was inserted into the HindIII-KpnI site of pcDV1 (Pharmacia).

pEXP118. COD1120 and COD1121 were annealed and inserted into the XbaI site of pEXP117. The orientation of the oligos is such that the re-created XbaI site is nearer the SV40 promoter than the KpnI and BglII sites. This creates a mammalian expression vector that uses the SV40 promoter.

pGT1. BglII fragment from lambda.clone.16 containing the genomic signal sequence of tPA was inserted into the BglII site of p31–63. The orientation of the signal sequence is such that it should direct the secretion of tPA.

pHY1. COD1198 and COD1199 were annealed and inserted into the BamHI-KpnI sites of pUC19 to make a plasmid containing a synthetic HypoA signal sequence.

pHY101. BamHI fragment from pUC19pcrTM-7 containing the 6EGFs was inserted into the BglII site of pHY1 to make a fusio coding sequence of the HypoA signal and the 6EGFs.

πvx.414. PstI fragment from p2G5 containing coding sequence for tPA was inserted into the PstI site of πvx.

pJAM1. XhoI-BamHI fragment from pBKL440X186 containing wild type BK enhancer (obtained from Suresh Subramani laboratory in La Jolla, Calif.) was inserted into the XhoI-BglII sites of pWHA148.

pMPSV-EH-CMV. Obtained from Harald Dinter at Schering AG in Berlin. Described in a Ph.D. thesis ("1988) by Petra Arteit in the lab of Hansjorg Hauser at the Cell Biology and Genetics Setion, GBF-Gesellshaft fur Biotechnologische Forschung mbH., D-3300 Braunschweig (F.R.G.). The parent plasmid pMPSV-EH (without the CMV) enhancer is described in Gene 68:213–219.

pPA003. BclI-BglII fragment from pVAC12 containing the genomic tPA signal and cDNA coding sequence of mature tPA inserted into the BglII site of pNEO5 so that tPA expression is driven by the triple LTR promoter.

pPA102. pPA003 was cut with BclI and XhoI, filled in with Klenow, and religated.

pDA129. ClaI-BglII fragment from pPA003 containing the genomic tPA signal sequence was inserted into the AsuII-BglII sites of pEXP118 so that expression of the tPA signal sequence is expressed off the SV40 promoter and contains the pcD intron between the promoter and the signal.

pPA133. COD1354 and COD1355 were annealed, cut with BamHI and BglII and inserted into the BglII site of pPA129. The orientation of the fragment is such that the unique reconstructed BglII site is close to the SV40 promoter.

pPA502. pHMR272 was cut with HindIII, filled in with Klenow, ligated to BamHI linkers, and then cut with BamHI. The BamHI fragment containing the hygromycin B gene was ligated into the BamHI site of pPA102. The orientation of the coding sequence of the hygromycin B gene is opposite to that of the tPA coding sequence.

pPA509. ClaI fragment from pSC662 containing the DHFR expression cassette was inserted into the non-methylated ClaI site of pPA502. The orientation of the coding sequence of the DHFR gene is opposite to that of the tPA gene.

pPA510. ClaI fragment from pPA509 containing the DHFR expression cassette was inserted back into the non-methylated ClaI site of pPA509. The coding sequence of the DHFR gene is in the same orientation as the tPA gene.

pSC614. HpaII-HindIII fragment of SV40 containing the SV40 promoters was inserted into the ClaI-HindIII sites of pSV200-dhfr to make a mammalian expression plasmid in which the expression of the DHFR gene is driven by the SV40 early promoter and which employs the SV40 polyA sequence. Note: This plasmid was previously called pSV201-dhfr.

pSC651. COD339 and COD340 were annealed and inserted into the BamHI site of pUC18. The orientation is such that the new ClaI site is situated between the EcoRI and BamHI sites of the new polylinker.

pSC652. COD339 and COD340 were annealed and inserted into the BamHI site of pUC18. The orientation is such that the new ClaI site is situated between the HindIII and BamHI sites of the new polylinker.

pSC661. PvuII-BamHI fragment of pSC614 containing the SV40 promoter, DHFR coding sequence, and the SV40 polyA sequence was inserted into the EcoRV-BamHI sites of pBR327.

pSC662. EcoRI-BamHI fragment of pSC661 containing the SV40 promoter, DHFR coding sequence, and the SV40 polyA sequence was inserted into the EcoRI-BamHI sites of pSC652 to make a plasmid containing the DHFR expression cassette on a ClaI fragment.

pSC709. COD1354 and COD1355 were annealed and inserted into the EcoRI-HindIII sites of pSC651.

pSC714. pVL1393 was cut with BglII, filled in, and religated to create a ClaI site.

pSC716. BamHI-EcoRI fragment from pHY1 containing the hypoA signal sequence was inserted into the BamHI-EcoRI sites of pSC714 to make a baculovirus expression plasmid that uses the polyhedron promoter and the hypoA signal sequence.

pSV200dhfr. HindIII-BamHI fragment from pSV2-dhfr (obtained from Paul Berg) containing the DHFR coding sequence with no promoter was inserted into the HindIII-BamHI sites of pBR328.

pTHR5. XhoI-NotI fragment of pPA133 containing the tPA signal sequence was inserted into the XhoI-NotI sites of pCDM8. This plasmid contains the tPA signal sequence and is suitable for transient transfections.

pTHR9. BamHI/NotI digest of PCR 127 fragment, which contains the 6 EGF region of thrombomodulin with the synthetic O-linked domain attached, was inserted into the BamHI-NotI sites of pBluescriptIISK+ (Stratagene). The PCR fragment was first obtained using COD1034 and COD1505, and template DNA was prepared by digesting pTM1.5 and pTM301 with ApaI, then ligating. Note: The sequence of the BssHII site, which should have been TTGCGCGCCA (SEQ ID NO:1) is actually TTGCgcGCGCCA (SEQ ID NO:2). Thus, the last part of the 6th EGF+O-linked domain is out of reading frame.

pTHR13. BamHI-BglII fragment of pTM301 containing 6EGF(+) of thrombomodulin was inserted into the BglII site of pTHR5. This plasmid contains the tPA signal sequence followed by 6EGFs of thrombomodulin in a plasmid suitable for transient and stable transfections.

pTHR14. AseI-ScaI fragment of pC21-2.3 kb (plasmid containing TGFbeta2 in pEMBL8+) containing the F1 ori was inserted into the NdeI-ScaI sites of pTMHY101 to make a baculovirus expression plasmid containing the F1 ori that expresses the 6EGFs.

pTHR23. BamHI-NotI fragment of pTHR9 containing 6EGF +O-linked domain inserted into BglII-NotI sites of pSC716. Note: This plasmid has an extra GC inserted in the BSSH2 site which puts the O-linked domain out of reading frame.

pTHR28. COD1573 was used for in vitro mutagenesis to convert the met388 of thrombomodulin to a leu in pTHR14. This created a PvuII site.

pTHR77. AseI-ScaI fragment from pUC9tet containing the Tet$^r$ gene and part of the Amp$^r$ gene inserted into the NdeI-ScaI sites of pTHR14 to make a baculovirus expression plasmid containing the f1 origin of replication and both the Amp$^r$ and Tet$^r$ genes.

pTHR78. pTHR23 cut with NdeI and BssHII and religated. This deleted the GC within the BssHII site that put the O-linked region of pTHR23 out of frame with the 6EGFs, thus correcting the reading frame.

pTHR87. COD1632 was used in in vitro mutagenesis to cause a frame shift mutation in the Amp gene of pTHR77 and to change the n-1 position of the signal cleavage site to proline. This created a new mutagenesis vector that would have positive selection (ampicillin resistance) when COD1633 is used in conjunction with the other primer.

pTHR121. NdeI-PstI (partial) fragment from pTM301 containing all of the 6EGFs inserted into the AsnI-PstI sites of pKT279 to put the 6EGFs under control of the Amp signal sequence.

pTHR127. BamHI-NheI fragment of pTHR28 containing the Met388→Leu mutation inserted into the BamHI-NheI sites of pTHR78 to make a 6EGFs-O-linked baculovirus expression plasmid with the met388→leu mutation.

pTHR130. MluI-BglII fragment of pTHR28 containing the met388→leu mutation inserted into the MluI-BglII sites of pTM301 to make a 6EGFs fragment in pUC that contains the met388→leu mutation.

pTHR161. EcoRV-BglII fragment from pTHR121 containing the 6EGFs inserted into the EcoRV-BamHI sites of pSELECT1(TM) to make an *E. coli* 6EGFs expression plasmid that can be used for in vitro mutagenesis.

pTHR211. ScaI-SacI fragment from pGEM3zf-containing the f1 origin of replication inserted into the ScaI-SacI sites of pTHR161. This is a new mutagenesis vector that uses the opposite strand as pTHR161.

pTHR219. MluI-NotI from pTHR127 containing the O-linked regions and the met388→leu mutation inserted into the MluI-NotI sites of pTHR161 in order to make an *E. coli* expression vector that expresses the 6EGFs-O-linked and that can be used for in vitro mutagenesis.

pTHR235. MluI-NotI fragment from pTHR219 containing the 6EGFs-O-linked into the MluI-NotI sites of pTHR211 containing the f1 ori in the opposite orientation as in pTHR219. This new plasmid is for in vitro mutagenesis of the O-linked and 6EGFs regions of thrombomodulin.

pTHR282. A ~6.8 kb HindIII fragment cloned into the HindIII site of pUC19. This fragment was obtained from a human chromosome 20 phage lambda library (ATCC 57712) and contains the full length TM gene. The fragment was originally detected in lambda plaque 7A-1. The fragment is cloned in the opposite orientation as pTHR283. Sequencing has shown that the orientation of the thrombomodulin gene is in the opposite orientation as the β-galactosidase gene.

pTHR293. HindIII fragment of pTHR282 containing the full length thrombomodulin gene cloned into the HindIII site of pSELECT1(TM). The fragment is oriented so that the thrombomodulin gene is in the opposite orientation as the β-galactosidase gene.

pTHR305. BamHI-NheI fragment from pTHR293 containing the amino terminal region of the thrombomodulin gene inserted into the BamHI-NheI sites of pTHR127 to make a baculovirus expression plasmid expressing the DNFL thrombomodulin.

pTHR312. NarI-NotI of pTHR130 containing thrombomodulin inserted into the NarI-NotI sites of pTHR13 to make a COS1 expression plasmid expressing thrombomodulin met388→leu.

pTHR316. BamHI fragment from pPA510 containing the tissue plasminogen activator (tPA) gene inserted into the BamHI site of pSELECT1(TM). The tPA gene is oriented in the opposite orientation as the Amp$^r$ gene.

pTHR321. ClaI-BssHII (partial) fragment containing the entire DNFL coding sequence with 15 bases of 5'-untranslated from pTHR305 inserted into the BssHII-ClaI sites of pWHA148.

pTHR322. ClaI-BssHII (partial) fragment containing the entire DNFL coding sequence with 15 bases of 5' untranslated from pTHR305 inserted into the BssHII-AccI sites of pWHA148.

pTHR324. HindIII-NotI fragment from pTHR322 containing the DNFL thrombomodulin gene inserted into the HindIII-NotI sites of pRcCMV for expression of DNFL in COS1 cells.

pTHR325. BamHI fragment from pPA510 containing the tPA gene inserted into the BamHI site of pSELECT1(TM). The tPA gene is oriented in the same orientation as the Amp$^r$ gene.

pTHR329. Eco47III-NotI fragment from pTHR235 containing the 6EGFs-O-linked and the met388→leu mutation inserted into the Eco47III-NotI sites of pTHR324. This gives us a COS1 expression vector containing DNFL with the met388→leu mutation.

pTHR330. HincII fragment from pTHRE316 containing the tPA gene inserted into the HincII sites of pWHA187. The orientation of the HincII fragments are such that the Amp gene is active.

pTHR333. EcoRI deletion of pTHR330.

pTHR348. COD1795 was used in in vitro mutagenesis to create a NotI site downstream of the C-terminus of the tPA gene in pTHR333. Note: pTHR333 (and pTHR348) does not contain the whole tPA gene. Also, COD1772 was used to change Tet$^s$ to Tet$^r$. This created a BamHI site.

pTHR350. StuI-XhoI fragment from pTHR348 containing the NotI site following the C-terminus of tPA inserted into the StuI-XhoI sites of pTHR325.

pTHR355. SpeI-XhoI fragment from pTHR350 containing the NotI site inserted into the SpeI-XhoI sites of pPA509 to make the equivalent of pPA509 having a NotI site immediately downstream of the tPA gene.

pTHR358. NarI-NotI fragment from pTHR235 containing the O-link region was ligated to the NarI-NotI vector fragment of pTHR312. The ligation reaction was then cut with SpeI-NotI and the fragment containing the O-link region was ligated into the SpeI-NotI sites of pTHR353 to make a mammalian expression vector that expresses the 6EGFs-O-link by means of the triple LTR promoter.

pTHR359. NruI-NotI fragment of pTHR329 (a COS1 expression plasmid) containing the DNFL gene and the CMV promoter inserted into the PvuII-NotI sites of pTHR353 to make a mammalian expression vector that expresses the DNFL gene off the CMV promoter.

pTHR371. SmaI-AatII fragment of pUC9 containing an EcoRI site into the EcoRV-AatII sites of pTHR322. This creates a plasmid with the DNFL gene on an EcoRI cassette.

pTHR375. PvuI fragment of pPA509 containing the triple LTRs inserted into a PvuI partial fragment of pTHR359 that contains the entire HygB gene and the origin of replication. This makes a new plasmid that expresses DNFL by means of the triple LTR promoter and the thrombomodulin signal sequence. This vector can be used for making stable clones and for transient expression in COS cells.

pTHR377. EcoRI fragment from pTHR371 containing the DNFL gene into the EcoRI site of pEXP6. The DNFL gene is oriented so that it's expression will be driven by the major late promoter of Adenovirus2.

pTHR384. EcoRV-KpnI fragment of pTHR377 containing the major late promoter of Adenovirus2 and the DNFL gene inserted into the PvuII-KpnI sites of pTHR358 to make a mammalian expression vector expressing the DNFL gene with the major late promoter, the BKV enhancer, the tripartite leader, and both VAI and VAII.

pTHR399. SmaI-KpnI fragment from pTHR329 containing met388→L inserted into the SmaI-KpnI sites of pTHR384.

pTHR438. EcoRI-NheI fragment from pTHR399 containing the front end of DNFL inserted into the EcoRI-NheI sites of pTHR321. A mixed plasmid population was then cut with EcoRI-HindIII and the fragment containing DNFL was inserted into the EcoRI-HindIII sites of pMPSV-EH-CMV (obtained from Harald Dinter at Schering).

pTHR469. PvuII deletion of pTHR375, cutting out the 3LTR's and most of the 6 EGF's, leaving the 6th EGF and the O-linked region.

pTR470. HindIII fragment from pTHR359 containing the SV40 promoter inserted into the HindIII site of pTHR359 to make an expression plasmid in which the expression of the DNFL gene is driven by the SV40 early promoter and that of the DHFR gene is driven by the SV40 late promoter.

pTHR482. HindIII-EcoRI from pTHR438 containing DNFL inserted into the HindIII-EcoRI sites of pBBS32. This creates a MPSV-EH-CMV and DNFL cassette in pBluescriptIISK+.

pTHR483. SspI-RsrII fragment of pTHR482, containing the MPSV-EH-CMV and DNFL cassette, inserted into the PvuII-PpuMI sites of pTHR469. This creates a plasmid for stable expression of DNFL in mammalian cells.

pTHR491. COD2218 was used to convert arg456 to gly and his457 to gln by in vitro mutagenesis in the vector pTHR235. This created a MscI site. Also, COD1886 was used to convert ser474 to ala to eliminate a potential GAG site in the O-link domain. This created a NarI site. Also, COD1689 was used to convert Amp$^s$ to Amp$^r$. This created a PstI site. This creates a DNFL molecule that should not be cleaved in CHO cells.

pTHR498. XbaI-SalI fragment from pTHR483 containing the DNFL gene inserted into the XbaI-SalI sites of pBBS37 to make a mammalian expression plasmid that expresses DNFL using the MPSV promoter-CMV enhancer and has the DHFR gene expressed off the SV40 late promoter. This plasmid also contains the hygromycin B gene.

pTHR500. AgeI-EspI fragment of pTHR483 containing part of the DNFL and the CMV enhancer region inserted into the AgeI-EspI sites of pTHR470. This creates a plasmid in which expression of the DNFL region is driven by the SV40 early promoter, with the CMV enhancer region situated after the DNFL coding region.

pTHR527. FspI fragment from pTHR483 containing the DNFL gene inserted into the FspI-PvuII sites of pUC18 to make a mammalian expression plasmid identical to pTHR483, except that it contains the pUC18 ori. This will result in higher plasmid copy number in E. coli.

pTHR550. FspI fragment from pTHR498 containing the DNFL gene into the SnaBI-FspI sites of pBBS61. The fragment is oriented so that the Amp gene is intact. This plasmid is ampicillin resistant, chloramphenicol resistant, and contains the f1 ori.

pTHR551. BamHI-BglII fragment from pBBS60 containing the PAC gene inserted into the BamHI site of pTHR550. The PAC gene is oriented in the same direction as the DHFR gene. An ApaI site restriction maps near the unique XcmI site.

pTM1.1. COD1127, COD1128, COD1129, COD1130, COD1131 were annealed and inserted into the EcoRI-HindIII sites of pUC18.

pTM1.2. COD1246 and COD1247 were annealed and inserted into the HindIII-EcoRI sites of pUC18.

pTM1.4. BssHII-SacII fragment from pTM1.1 containing the thrombomodulin coding sequence inserted into the BssHII-SacII sites of pTM1.2.

pTM1.5. BssHII-HindIII fragment from pTM3.0-1.9 containing the thrombomodulin coding sequence inserted into the BssHII-HindIII sites of pTM1.4. Note: Sequence analysis showed that the BssHII site contained an extra gc, making its sequence gcgcgcgc.

pTM3.0-19. COD1169, COD1170, COD1171, COD1172, COD1173 were annealed and inserted into the EcoRI-HindIII sites of pUC18.

pTM301. BamHI-NotI fragment of a PCR product, generated using COD1034 and COD1411 as PCR primers and pUC19pcrTM-7 as the template, that contains the 6EGFs, inserted into the BamHI-NotI sites of pSC709.

pTMHY101. BamHI-EcoRI fragment from pHY101 containing the hypoA signal sequence fused to the 6EGFs inserted into the BamHI-EcoRI sites of pVL1393 (Invitrogen) to make a baculovirus expression plasmid that expresses the 6EGFs.

pUC19pcrTM-7. PCR fragment containing the 6EGFs, generated using COD1033 and COD1034 as primers and CHL-1 genomic DNA as a template, blunt-end cloned into the SmaI site of pUC19. The 6EGFs coding sequence is in the opposite orientation as the β-galactosidase promoter.

pUC9tet. Obtained from Pharmacia.

pVAC12. NarI fragment from p31-63-44 containing the genomic signal sequence of tPA inserted into the NarI site of p31-2. The signal sequence is oriented so as to direct the secretion of tPA. Note: This plasmid contains the signal and mature sequence on a BclI-BglII (partial) cassette.

pWHA70. HindIII-KpnI fragment from lambda.TPA.14 containing the coding sequence for mature tPA inserted into the HindIII-KpnI sites of pUC19. The coding sequence for tPA is oriented in the same direction as the β-galactosidase promoter.

pWHA72. XhoII fragment from pWHA70 containing the coding sequence mature tPA inserted into the BaHI site of pUC8. The coding sequence for tPA is oriented in the opposite direction as the β-galactosidase promoter.

pWHA148. COD316 and COD317 were annealed and inserted into the HindIII site of pUC18. The orientation of the fragment is such that the unique StuI site is closer to the unique EcoRI site than the unique HindIII site.

pWHA187. Mutagenized pSELECT1(TM) using the following oligos: COD1690 to mutate the Amp gene to resistant and creating a PstI site. COD1771 to mutate the Tet gene to sensitive and creating an AccI site. COD1778 to add multiple restriction sites (including a BglII site) just upstream of the Amp gene. COD1779 to add a BclI site just downstream of the Tet gene.

Oligonucleotides

COD316 (SEQ ID NO:3)
AGCTCCAGGCCTGGCGCGC-GAGATCTCGGGCCCGATCGATGCCGCG-GCGATATCGCT CGAGGA

COD317 (SEQ ID NO:4)
AGCTTCCTCGAGCGATATCGCCGCG-GCATCGATCGGGCCCGAGATCTCGCGCGCCAG GCCTGG

COD393 (SEQ ID NO:5)
GATCAATCGATG

COD340 (SEQ ID NO:6)
GATCCATCGATT

COD1033 (SEQ ID NO:7)
CCGGGATCCTCAACAGTCGGTGCCAATGTGGCG

COD1034 (SEQ ID NO:8)
CCGGGATCCTGCAGCGTGGAGAACGGCGGCTGC

COD1120 (SEQ ID NO:9)
CTAGAACGCGTTTCGAAAGATCTC

COD1121 (SEQ ID NO:10)
CTAGGAGATCTTTCGAAACGCGTT

COD1127 (SEQ ID NO:11)
AGCTTACAGTCGGTGCCAATGTGGCGCG-CAAGGGCCCGAGTCGGGCCCGCAGATGCA

COD1128 (SEQ ID NO:12)
TCACAGCTAGCCTGGGTGTTGGGGTCG-CAGTCCGCGGGACAGGCAGTCTGGTGCAG

COD1129 (SEQ ID NO:13)
AATTCTGCAACCAGACTGCCTGTC-CCGCGGACTGCGACCCCAACACCCAGGCTAGCT GTGAGTGCCCTGAAGGCTACATCCTG-GACGACGGTTTCATCTGCACGGACATCGAC

COD1130 (SEQ ID NO:14)
GAGTGCGAAAACGGCGGCTTCTGCTC-CGGGGTGTGCCACAACCTCCCCGGAACGTTC GAGTGCATCTCGCGGGCCCCGACTCGGC-CCTTGCGCGCCACATTGGCACCGACTGTA

COD1131 (SEQ ID NO:15)
CTCGAACGTTCCGGGGAGGTTGTGGCA-CACCCCGGAGCAGAAGCCGCCGTTTTCGCA CTCGTCGATGTCCGTGCAGATGAAAC-CGTCGTCCAGGATGTAGCCTTCAGGGCAC

COD1169 (SEQ ID NO:16)
AATTCGGGCCCGACTCGGCCCT-TGCGCGCCACATTGGCACCGACTGTGACTCCGGCA AGGTGGACGGTGGCGACAGCGG

COD1170 (SEQ ID NO:17)
CTCTGGCGAGCCCCGCCCAGCCCGACGC-CCGGCTCCACCTTGACTCCTCCGGGGGGG CCGTGGGGCTCGTGCATTCGTGAA

COD1171 (SEQ ID NO:18)
AGCTTTCACGAATGCACGAGCCCCACG-GCCGGAGGAGTC

COD1172 (SEQ ID NO:19)
AAGGTGGAGC-CCGGGCGTCGGGCTGGGCGGGGGCTCGC-CAGAGCCGCTGTCGCCACC GTCCACCTTGCCG-GAGTCACAG

COD1173 (SEQ ID NO:20)
TCGGTGCCAATGTGGCGCGCAAGGGC-CGAGTCGGGCCCG

COD1198 (SEQ ID NO:21)
GATCCATGCTCAAGTTTGTTATTTTAT-TGTGCAGTATTGCCTATGTTTTCGGTGCCG TCG-TACCAAGATCTCCCCGGGTAC

COD1199 (SEQ ID NO:22)
CCGGGGAGATCTTGGTACGACGGCAC-CGAAAACATAGGCAATACTGCACAATAAAAT AACAAACTTGAGCATG

COD1246 (SEQ ID NO:23)
AATTCAGATCTTGCAACCAGACTGCCT-GTCCCGCGGACGCCCTTGCGCCACATTGGC ACCGACTGTTGAAGATCTA

COD1247 (SEQ ID NO:24)
AGCTTAGATCTTCAACAGTCGGTGC-CAATGTGGCGCGCAAGGGCGTCCGCGGGACAG GCAGTCTGGTTGCAAGATCTG

COD1354 (SEQ ID NO:25)
AGCTCAGATCTGGCGGCCGCAATACG-TACCGTACGGGGATCC

COD1355 (SEQ ID NO:26)
AATTGGATCCCCGTACGGTACGTAT-TGCGGCCGCCAGATCTG

COD1411 (SEQ ID NO:27)
ATGCGGCCGCTCAACAGTCGGTGCCAAT-GTGGCG

COD1505 (SEQ ID NO:28)
CCTGCGGCCGCTCACGAATGCACGAGC-CCCACGGCCGGA

COD1573 (SEQ ID NO:29)
CCCCACGAGCCCGCACAGGTGCCAGCT-GTTTTGCAACCAGACTGCCTGTCCAGCCG

COD1624 (SEQ ID NO:30)
GACTGCCTGTCCAGCCCGACTG

COD1632 (SEQ ID NO:31)
CAGCATCTTTTACTTTCAC-CAGCGTTTCTGTGGTGAGGAAAAACAG-GAAGGCAAAAT GCCGC

COD1633 (SEQ ID NO:32)
CAGCATCTTTTACTTTCAC-CAGCGTTTCTGGGTGCGCAAAAACAG-GAAGGCAAAATG CCGC

COD1689 (SEQ ID NO:33)
GACCACGATGCCTGCAGCAATGGCAAC

COD1690 (SEQ ID NO:34)
GTTCGCCATTGCTGCAGGCATCGTGGTC

COD1771 (SEQ ID NO:35)
CCACACCCGTCCTGTGATTGTCTACGC-CCGGACGC

COD1772 (SEQ ID NO:36)
CCACACCCGTCCTGTGGATCCTCTACGC-CGGACGC

COD1778 (SEQ ID NO:37)
GAGTGCACCATATGCGGTGT-GAGATCTCGTACGCACGTGCCTCGAG-TACGTACCGCA TCAGGCG

COD1779 (SEQ ID NO:38)
GGTGCGCATGATCATGCTCCTGTCG

COD1795 (SEQ ID NO:39)
CATGCGACCGTGAGCGGCCGCACCCGACTCCTC

COD1886 (SEQ ID NO:40)
GGCGACAGCGGCGCCGGCGAGCCCCCG

COD1940 (SEQ ID NO:41)
GATGAATGCTCATCCCGAGTTCCGTATGGCA

COD1941 (SEQ ID NO:42)

GATGAATGCTCATGATTCCGTATGGCA

COD2168 (SEQ ID NO:43)

CTATAGATCTAATATTG-
GCTCTAGTTTTGACTCAACAATATC

COD2169 (SEQ ID NO:44)

TTGCGGGCCCATCGGTCCGCTGGGTG-
GAGACTTGGAAATCCCCGTGAGT

COD2218 (SEQ ID NO:45)

GACTCGGCCCTTGCTGGCCAGATTG-
GCACCGACTG

COD2461 (SEQ ID NO:46)

CCAGCGTTTCTGGGTGCGCAAAAACAGGAAG

COD2588 (SEQ ID NO:47)

GCAGCCAAGCTTTGGCGTAATCATGGTC

COD2606 (SEQ ID NO:48)

CACGAGGCCCTTTCGTCTTCGATCCAGA-
CATGATAAGATAC

COD2607 (SEQ ID NO:49)

CACCGGTCGTGGCGGCCGACGGCCTC-
CAAAAAGCCTCCTCAC

COD2609 (SEQ ID NO:50)

GCTCGATGTGGCGGTCAGGGTCCACTG-
TATGGCGTGTTGCAGGGTAGTCGGCGAACG

COD2610 (SEQ ID NO:51)

GCCCTGAGCTGTCCCCCCCCCAGGCTT-
TAATGCGGTAGTTTATC

Although the foregoing invention has been described in detail for purposes of clarity of understanding, it will be obvious that certain modifications may be practiced within the scope of the appended claims.

---

What is claimed is:

1. A method for introducing a plurality of mutations to a nucleic acid construct comprising a target sequence, a first marker sequence encoding a first protein having an inoperable first marker activity, and a second marker sequence encoding a second protein having an operable second marker activity, said method comprising the steps of:

(a) annealing to a single-stranded form of said nucleic acid construct a first oligonucleotide having a sequence substantially complementary to a portion of said nucleic acid construct, wherein the sequence of said first oligonucleotide is selected so as to change a nucleotide at a first position of said nucleic acid construct where said first position is within said target sequence, and to introduce or remove a first restriction site at a second position of said nucleic acid construct;

a second oligonucleotide having a sequence substantially complementary to a portion of said nucleic acid construct, wherein the sequence of said second oligonucleotide is selected so as to change one or more nucleotides in said first marker sequence to produce a mutated first marker sequence in a manner which results in an operable first marker activity; and a third oligonucleotide having a sequence substantially complementary to a portion of said nucleic acid construct, wherein the sequence of said third oligonucleotide is selected so as to change one or more nucleotides in said second marker sequence to produce a mutated second marker sequence in a manner which results in an inoperable second marker activity, thereby forming a primary annealed product;

(b) transforming a host cell with said primary annealed product;

(c) screening or selecting progeny of transformed host cells having said operable first marker activity;

(d) identifying progeny screened or selected and containing a mutated nucleic acid construct containing a mutated target sequence and having said introduced or removed first restriction site;

(e) annealing to a single-stranded form of said mutated nucleic acid construct a fourth oligonucleotide having a sequence substantially complementary to a portion of said mutated nucleic acid construct, wherein the sequence of said fourth oligonucleotide is selected so as to change a nucleotide at a first position of said mutated nucleic acid construct where said first position is within said mutated target sequence, and to introduce or remove a second restriction site at a second position of said mutated nucleic acid construct;

a fifth oligonucleotide having a sequence substantially complementary to a portion of said mutated nucleic acid construct, wherein the sequence of said fifth oligonucleotide is selected so as to restore said first marker sequence in a manner which results in said inoperable first marker activity; and a sixth oligonucleotide having a sequence substantially complementary to a portion of said mutated nucleic acid construct, wherein the sequence of said sixth oligonucleotide is selected so as to restore said second marker sequence in a manner which results in said operable second marker activity, thereby forming a secondary annealed product;

(f) transforming a host cell with said secondary annealed product;

(g) screening or selecting progeny of transformed host cells having said operable second marker activity; and (h) identifying progeny screened or selected and containing a further mutated nucleic acid construct having said introduced or removed second restriction site.

2. The method of claim 1 wherein said target sequence encodes a polypeptide.

3. The method of claim 2 wherein said target sequence encoding a polypeptide is operably linked to a promoter.

4. The method of claim 1 wherein said target sequence encodes a polypeptide and the sequences of both said first and fourth oligonucleotides are each selected so as to change one or more nucleotides in said target sequence in a manner which results in a change in an amino acid of said polypeptide encoded by said target sequence, and to introduce or remove a restriction site from said nucleic acid construct in a manner which does not result in a change in an amino acid of said polypeptide.

5. The method of claim 1 further comprising the step of extending said first, second, and third oligonucleotides with a DNA polymerase.

6. The method of claim 1 further comprising the step of adding a DNA ligase.

7. The method of claim 1 wherein said nucleic acid construct comprises:

(a) A ColE1 origin of replication;

(b) An M13 or f1 phage origin of replication; and (c) A polylinker situated within a lacZ gene.

8. The method of claim 1 wherein said target sequence encodes a polypeptide and said target sequence is operably linked to a eukaryotic promoter and said nucleic acid construct further comprises a marker for selecting eukaryotic cells into which said nucleic acid construct is introduced.

9. The method of claim 1 wherein said nucleic acid construct is pBBS82, pBBS83, pBBS92, pBBS95, pBBS96, pBBS97, pBBS98, pBBS99, pBBS100, pBBS101, pBBS104, pBBS121, pBBS122, pBBS124, pBBS125, pBBS135, pBBS141, or pBBS145.

10. The method of claim 1 wherein said first oligonucleotide in step (a) is selected so as to change one or more nucleotides at a plurality of positions within said target sequence, and wherein said fourth oligonucleotide in step(e) is selected so as to change one or more nucleotides at a plurality of positions within said mutated target sequence.

11. A kit for introducing one or more mutations to a nucleic acid construct comprising:

(a) said nucleic acid construct comprising a ColE1 origin of replication, a polylinker within a lacZ gene for inserting a target sequence, a first marker sequence encoding a first protein having an inoperable first marker activity, and a second marker sequence encoding a second protein having an operable second marker activity;

(b) a first oligonucleotide having a sequence substantially complementary to a portion of said nucleic acid construct, wherein the sequence of said first oligonucleotide is selected so as to change one or more nucleotides in said first marker sequence to produce a mutated first marker sequence in a manner which results in an operable first marker activity;

(c) a second oligonucleotide having a sequence substantially complementary to a portion of said nucleic acid construct, wherein the sequence of said second oligonucleotide is selected so as to change one or more nucleotides in said second marker sequence to produce a mutated second marker sequence which results in an inoperable second marker activity;

(d) a third oligonucleotide having a sequence substantially complementary to a portion of said nucleic acid construct, wherein the sequence of said third oligonucleotide is selected so as to restore said first marker sequence in a manner which results in said inoperable first marker activity;

(e) a fourth oligonucleotide having a sequence substantially complementary to a portion of said nucleic acid construct, wherein the sequence of said fourth oligonucleotide is selected so as to restore said second marker sequence in a manner which results in said operable second marker activity;

(f) a DNA polymerase;

(g) deoxyribonucleotides;

(h) a DNA ligase: and (i) buffers suitable for activity of said DNA polymerase and said DNA ligase.

12. The kit of claim 11 wherein said nucleic acid construct is pBBS82, pBBS83, pBBS92, pBBS95, pBBS96, pBBS97, pBBS98, pBBS99, pBBS100, pBBS101, pBBS104, pBBS121, pBBS122, pBBS124, pBBS125, pBBS135, pBBS141, or pBBS145.

* * * * *

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

TTGCGCGCCA                                                                                          10

( 2 ) INFORMATION FOR SEQ ID NO:2:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TTGCGCGCGC CA                                                                                       12

( 2 ) INFORMATION FOR SEQ ID NO:3:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

AGCTCCAGGC CTGGCGCGCG AGATCTCGGG CCCGATCGAT GCCGCGGCGA TATCGCTCGA          60

GGA                                                                                                 63

( 2 ) INFORMATION FOR SEQ ID NO:4:

( i ) SEQUENCE CHARACTERISTICS:
( A ) LENGTH: 63 base pairs
( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGCTTCCTCG AGCGATATCG CCGCGGCATC GATCGGGCCC GAGATCTCGC GCGCCAGGCC    60

TGG    63

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GATCAATCGA TG    12

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GATCCATCGA TT    12

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CCGGGATCCT CAACAGTCGG TGCCAATGTG GCG    33

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCGGGATCCT GCAGCGTGGA GAACGGCGGC TGC    33

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CTAGAACGCG TTTCGAAAGA TCTC      24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CTAGGAGATC TTTCGAAACG CGTT      24

( 2 ) INFORMATION FOR SEQ ID NO:11:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AGCTTACAGT CGGTCCCAAT GTGGCGCGCA AGGGCCCGAG TCGGGCCCGC AGATGCA      57

( 2 ) INFORMATION FOR SEQ ID NO:12:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TCACAGCTAG CCTGGGTGTT GGGGTCGCAG TCCGCGGGAC AGGCAGTCTG GTGCAG      56

( 2 ) INFORMATION FOR SEQ ID NO:13:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AATTCTGCAA CCAGACTGCC TGTCCCGCGG ACTGCGACCC CAACACCCAG GCTAGCTGTG      60

AGTGCCCTGA AGGCTACATC CTGGACGACG GTTTCATCTG CACGGACATC GAC      113

( 2 ) INFORMATION FOR SEQ ID NO:14:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GAGTGCGAAA  ACGGCGGCTT  CTGCTCCGGG  GTGTGCCACA  ACCTCCCCGG  AACGTTCGAG        60

TGCATCTCGC  GGGCCCCGAC  TCGGCCCTTG  CGCGCCACAT  GGCACCGAC   TGTA             114
```

( 2 ) INFORMATION FOR SEQ ID NO:15:

( i ) SEQUENCE CHARACTERISTICS:
        ( A ) LENGTH: 112 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CTCGAACGTT  CCGGGGAGGT  TGTGGCACAC  CCCGGAGCAG  AAGCCGCCGT  TTTCGCACTC        60

GTCGATGTCC  GTGCAGATGA  AACCGTCGTC  CAGGATGTAG  CCTTCAGGGC  AC               112
```

( 2 ) INFORMATION FOR SEQ ID NO:16:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
AATTCGGGCC  CGACTCGGCC  CTTGCGCGCC  ACATTGGCAC  CGACTGTGAC  TCCGGCAAGG        60

TGGACGGTGG  CGACAGCGG                                                         79
```

( 2 ) INFORMATION FOR SEQ ID NO:17:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
CTCTGGCGAG  CCCCGCCCAG  CCCGACGCCC  GGCTCCACCT  TGACTCCTCC  GGGGGGCCG         60

TGGGGCTCGT  GCATTCGTGA  A                                                     81
```

( 2 ) INFORMATION FOR SEQ ID NO:18:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
AGCTTTCACG  AATGCACGAG  CCCCACGGCC  GGAGGAGTC                                 39
```

( 2 ) INFORMATION FOR SEQ ID NO:19:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

```
AAGGTGGAGC CCGGGCGTCG GGCTGGGCGG GGGCTCGCCA GAGCCGCTGT CGCCACCGTC    60
CACCTTGCCC GAGTCACAG                                                 79
```

( 2 ) INFORMATION FOR SEQ ID NO:20:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

```
TCGGTGCCAA TGTGGCGCGC AAGGGCCGAG TCGGGCCCG                            39
```

( 2 ) INFORMATION FOR SEQ ID NO:21:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
GATCCATGCT CAAGTTTGTT ATTTTATTGT GCAGTATTGC CTATGTTTTC GGTGCCGTCG    60
TACCAAGATC TCCCCGGGTA C                                              81
```

( 2 ) INFORMATION FOR SEQ ID NO:22:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
CCGGGGAGAT CTTGGTACGA CGGCACCGAA AACATAGGCA ATACTGCACA ATAAAATAAC    60
AAACTTGAGC ATG                                                       73
```

( 2 ) INFORMATION FOR SEQ ID NO:23:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
AATTCAGATC TTGCAACCAG ACTGCCTGTC CCGCGGACGC CCTTGCGCCA CATTGGCACC    60
GACTGTTGAA GATCTA                                                    76
```

( 2 ) INFORMATION FOR SEQ ID NO:24:

( i ) SEQUENCE CHARACTERISTICS:
        ( A ) LENGTH: 78 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:24:

AGCTTAGATC TTCAACAGTC GGTGCCAATG TGGCGCGCAA GGGCGTCCGC GGGACAGGCA    60

GTCTGGTTGC AAGATCTG    78

(2) INFORMATION FOR SEQ ID NO:25:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:25:

AGCTCAGATC TGGCGGCCGC AATACGTACC GTACGGGGAT CC    42

(2) INFORMATION FOR SEQ ID NO:26:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:26:

AATTGGATCC CCGTACGGTA CGTATTGCGG CCGCCAGATC TG    42

(2) INFORMATION FOR SEQ ID NO:27:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:27:

A Y GCGGCCGC TCAACAGTGC GTGCCAATGT GGCG    34

(2) INFORMATION FOR SEQ ID NO:28:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:28:

CCTGCGGCCG CTCACGAATG CACGAGCCCC ACGGCCGGA    39

(2) INFORMATION FOR SEQ ID NO:29:

(i) SEQUENCE CHARACTERISTICS:
    (A) LENGTH: 55 base pairs
    (B) TYPE: nucleic acid
    (C) STRANDEDNESS: single
    (D) TOPOLOGY: linear ( i i ) MOLECULE TYPE: DNA (genomic)

( x i ) SEQUENCE DESCRIPTION: SEQ ID NO:29:

CCCCACGAGC CGCACAGGTG CCAGCTGTTT TGCAACCAGA CTGCCTGTCC AGCCG    55

( 2 ) INFORMATION FOR SEQ ID NO:30:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GACTGCCTGT CCAGCCCGAC TG    22

( 2 ) INFORMATION FOR SEQ ID NO:31:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

CAGCATCTTT TACTTTCACC AGCGTTTCTG TGGTGAGGAA AAACAGGAAG GCAAAATGCC    60

GC    62

( 2 ) INFORMATION FOR SEQ ID NO:32:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CAGCATCTTT TACTTTCACC AGCGTTTCTG GGTGCGCAAA AACAGGAAGG CAAAATGCCG    60

C    61

( 2 ) INFORMATION FOR SEQ ID NO:33:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GACCACGATG CCTGCAGCAA TGGCAAC    27

( 2 ) INFORMATION FOR SEQ ID NO:34:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GTTCGCCATT GCTGCAGGCA TCGTCGTC                                                              28

( 2 ) INFORMATION FOR SEQ ID NO:35:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

CCACACCCGT CCTGTGATTG TCTACGCCCG GACGC                                                      35

( 2 ) INFORMATION FOR SEQ ID NO:36:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

CCACACCCGT CCTGTGGATC CTCTACGCCG GACGC                                                      35

( 2 ) INFORMATION FOR SEQ ID NO:37:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GAGTGCACCA TATGCGGTGT GAGATCTCGT ACGCACGTGC CTCGAGTACG TACCGCATCA     60

GGCG                                                                 64

( 2 ) INFORMATION FOR SEQ ID NO:38:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

GGTCGGCATG ATCATGCTCC TGTCG                                                                 25

( 2 ) INFORMATION FOR SEQ ID NO:39:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

CATGCGACCG TGAGCGGCCG CACCCGACTC CTC    33

(2) INFORMATION FOR SEQ ID NO:40:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:40:

GGCGACAGCG GCGCCGGCGA GCCCCCG    27

(2) INFORMATION FOR SEQ ID NO:41:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:41:

GATGAATGCT CATCCCGAGT TCCGTATGGC A    31

(2) INFORMATION FOR SEQ ID NO:42:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:42:

GATGAATGCT CATGATTCCG TATGGCA    27

(2) INFORMATION FOR SEQ ID NO:43:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:43:

CTATAGATCT AATATTGGCT CTAGTTTTGA CTCAACAATA TC    42

(2) INFORMATION FOR SEQ ID NO:44:

(i) SEQUENCE CHARACTERISTICS:
    (A) LENGTH: 49 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:44:

TTGCGGGCCC ATCGGTCCGC TGGGTGGAGA CTTGGAAATC CCCGTGAGT    49

(2) INFORMATION FOR SEQ ID NO:45:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:45:

GACTCGGCCC TTGCTGGCCA GATTGGCACC GACTG     35

( 2 ) INFORMATION FOR SEQ ID NO:46:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:46:

CCAGCGTTTC TGGGTGCGCA AAAACAGGAA G     31

( 2 ) INFORMATION FOR SEQ ID NO:47:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:47:

GCAGCCAAGC TTTGGCGTAA TCATGGTC     28

( 2 ) INFORMATION FOR SEQ ID NO:48:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:48:

CACGAGGCCC TTTCGTCTTC GATCCAGACA TGATAAGATA C     41

( 2 ) INFORMATION FOR SEQ ID NO:49:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:49:

CACCGGTCGT GGCGGCCGAC GGCCTCCAAA AAGCCTCCTC AC     42

( 2 ) INFORMATION FOR SEQ ID NO:50:

( i ) SEQUENCE CHARACTERISTICS:
  ( A ) LENGTH: 57 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:50:

GCTCGATGTG GCGGTCAGGG TCCACTGTAT GGCGTGTTGC AGGGTAGTCG GCGAACG    57

( 2 ) INFORMATION FOR SEQ ID NO:51:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

GCCCTGAGCT GTCCCCCCCC CCAGGCTTTA ATGCGGTAGT TTATC    45

( 2 ) INFORMATION FOR SEQ ID NO:52:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:52:

TGCAGTCTAG ACCCGGGAAT TCGGGCCCGG ATC    33

( 2 ) INFORMATION FOR SEQ ID NO:53:

( i ) SEQUENCE CHARACTERISTICS:
        ( A ) LENGTH: 2011 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: sig_peptide
        ( B ) LOCATION: 147..204

( i x ) FEATURE:
        ( A ) NAME/KEY: CDS
        ( B ) LOCATION: 147..1871

( x i ) SEQUENCE DESCRIPTION: SEQ ID NO:53:

```
GGCAGCGCGC AGCGGCAAGA AGTGTCTGGG CTGGGACGGA CAGGAGAGGC TGTCGCCATC         60

GGCGTCCTGT GCCCCTCTGC TCCGGCACGG CCCTGTCGCA GTGCCCGCGC TTTCCCCGGC         120

GCCTGCACGC GGCGCGCCTG GGTAAC ATG CTT GGG GTC CTG GTC CTT GGC GCG         173
                             Met Leu Gly Val Leu Val Leu Gly Ala
                              1               5

CTG GCC CTG GCC GGC CTG GGG TTC CCC GCA CCC GCA GAG CCG CAG CCG          221
Leu Ala Leu Ala Gly Leu Gly Phe Pro Ala Pro Ala Glu Pro Gln Pro
 10              15                  20                  25

GGT GGC AGC CAG TGC GTC GAG CAC GAC TGC TCC GCG CTC TAC CCG GGC          269
Gly Gly Ser Gln Cys Val Glu His Asp Cys Ser Ala Leu Tyr Pro Gly
                 30                  35                  40

CCC GCG ACC TTC CTC AAT GCC AGT CAG ATC TGC GAC GGA CTG CGG GGC          317
Pro Ala Thr Phe Leu Asn Ala Ser Gln Ile Cys Asp Gly Leu Arg Gly
             45                  50                  55

CAC CTA ATG ACA GTG CGC TCC TCG GTG GCT GCC GAT GTC ATT TCC TTG          365
His Leu Met Thr Val Arg Ser Ser Val Ala Ala Asp Val Ile Ser Leu
```

|       |       |       |       |       |       |       |       |       |       |       |       |       |       |       |       |      |
|---|---|---|---|---|---|---|---|---|---|---|---|---|---|---|---|---|
|       |       |       | 60    |       |       |       |       | 65    |       |       |       |       | 70    |       |       |      |
| CTA   | CTG   | AAC   | GGC   | GAC   | GGC   | GGC   | GTT   | GGC   | CGC   | CGG   | CGC   | CTC   | TGG   | ATC   | GGC   | 413  |
| Leu   | Leu   | Asn   | Gly   | Asp   | Gly   | Gly   | Val   | Gly   | Arg   | Arg   | Arg   | Leu   | Trp   | Ile   | Gly   |      |
|       | 75    |       |       |       |       | 80    |       |       |       |       | 85    |       |       |       |       |      |
| CTG   | CAG   | CTG   | CCA   | CCC   | GGC   | TGC   | GGC   | GAC   | CCC   | AAG   | CGC   | CTC   | GGG   | CCC   | CTG   | 461  |
| Leu   | Gln   | Leu   | Pro   | Pro   | Gly   | Cys   | Gly   | Asp   | Pro   | Lys   | Arg   | Leu   | Gly   | Pro   | Leu   |      |
|       | 90    |       |       |       |       | 95    |       |       |       |       | 100   |       |       |       | 105   |      |
| CGC   | GGC   | TTC   | CAG   | TGG   | GTT   | ACG   | GGA   | GAC   | AAC   | AAC   | ACC   | AGC   | TAT   | AGC   | AGG   | 509  |
| Arg   | Gly   | Phe   | Gln   | Trp   | Val   | Thr   | Gly   | Asp   | Asn   | Asn   | Thr   | Ser   | Tyr   | Ser   | Arg   |      |
|       |       |       |       | 110   |       |       |       |       | 115   |       |       |       |       | 120   |       |      |
| TGG   | GCA   | CGG   | CTC   | GAC   | CTC   | AAT   | GGG   | GCT   | CCC   | CTC   | TGC   | GGC   | CCG   | TTG   | TGC   | 557  |
| Trp   | Ala   | Arg   | Leu   | Asp   | Leu   | Asn   | Gly   | Ala   | Pro   | Leu   | Cys   | Gly   | Pro   | Leu   | Cys   |      |
|       |       |       | 125   |       |       |       |       | 130   |       |       |       |       | 135   |       |       |      |
| GTC   | GCT   | GTC   | TCC   | GCT   | GCT   | GAG   | GCC   | ACT   | GTG   | CCC   | AGC   | GAG   | CCG   | ATC   | TGG   | 605  |
| Val   | Ala   | Val   | Ser   | Ala   | Ala   | Glu   | Ala   | Thr   | Val   | Pro   | Ser   | Glu   | Pro   | Ile   | Trp   |      |
|       |       |       | 140   |       |       |       |       | 145   |       |       |       |       | 150   |       |       |      |
| GAG   | GAG   | CAG   | CAG   | TGC   | GAA   | GTG   | AAG   | GCC   | GAT   | GGC   | TTC   | CTC   | TGC   | GAG   | TTC   | 653  |
| Glu   | Glu   | Gln   | Gln   | Cys   | Glu   | Val   | Lys   | Ala   | Asp   | Gly   | Phe   | Leu   | Cys   | Glu   | Phe   |      |
|       | 155   |       |       |       |       | 160   |       |       |       |       | 165   |       |       |       |       |      |
| CAC   | TTC   | CCA   | GCC   | ACC   | TGC   | AGG   | CCA   | CTG   | GCT   | GTG   | GAG   | CCC   | GGC   | GCC   | GCG   | 701  |
| His   | Phe   | Pro   | Ala   | Thr   | Cys   | Arg   | Pro   | Leu   | Ala   | Val   | Glu   | Pro   | Gly   | Ala   | Ala   |      |
| 170   |       |       |       |       | 175   |       |       |       |       | 180   |       |       |       |       | 185   |      |
| GCT   | GCC   | GCC   | GTC   | TCG   | ATC   | ACC   | TAC   | GGC   | ACC   | CCG   | TTC   | GCG   | GCC   | CGC   | GGA   | 749  |
| Ala   | Ala   | Ala   | Val   | Ser   | Ile   | Thr   | Tyr   | Gly   | Thr   | Pro   | Phe   | Ala   | Ala   | Arg   | Gly   |      |
|       |       |       |       | 190   |       |       |       |       | 195   |       |       |       |       | 200   |       |      |
| GCG   | GAC   | TTC   | CAG   | GCG   | CTG   | CCG   | GTG   | GGC   | AGC   | TCC   | GCC   | GCG   | GTG   | GCT   | CCC   | 797  |
| Ala   | Asp   | Phe   | Gln   | Ala   | Leu   | Pro   | Val   | Gly   | Ser   | Ser   | Ala   | Ala   | Val   | Ala   | Pro   |      |
|       |       |       | 205   |       |       |       |       | 210   |       |       |       |       | 215   |       |       |      |
| CTC   | GGC   | TTA   | CAG   | CTA   | ATG   | TGC   | ACC   | GCG   | CCG   | CCC   | GGA   | GCG   | GTC   | CAG   | GGG   | 845  |
| Leu   | Gly   | Leu   | Gln   | Leu   | Met   | Cys   | Thr   | Ala   | Pro   | Pro   | Gly   | Ala   | Val   | Gln   | Gly   |      |
|       |       | 220   |       |       |       |       | 225   |       |       |       |       | 230   |       |       |       |      |
| CAC   | TGG   | GCC   | AGG   | GAG   | GCG   | CCG   | GGC   | GCT   | TGG   | GAC   | TGC   | AGC   | GTG   | GAG   | AAC   | 893  |
| His   | Trp   | Ala   | Arg   | Glu   | Ala   | Pro   | Gly   | Ala   | Trp   | Asp   | Cys   | Ser   | Val   | Glu   | Asn   |      |
|       | 235   |       |       |       |       | 240   |       |       |       |       | 245   |       |       |       |       |      |
| GGC   | GGC   | TGC   | GAG   | CAC   | GCG   | TGC   | AAT   | GCG   | ATC   | CCT   | GGG   | GCT   | CCC   | CGC   | TGC   | 941  |
| Gly   | Gly   | Cys   | Glu   | His   | Ala   | Cys   | Asn   | Ala   | Ile   | Pro   | Gly   | Ala   | Pro   | Arg   | Cys   |      |
| 250   |       |       |       |       | 255   |       |       |       |       | 260   |       |       |       |       | 265   |      |
| CAG   | TGC   | CCA   | GCC   | GGC   | GCC   | GCC   | CTG   | CAG   | GCA   | GAC   | GGG   | CGC   | TCC   | TGC   | ACC   | 989  |
| Gln   | Cys   | Pro   | Ala   | Gly   | Ala   | Ala   | Leu   | Gln   | Ala   | Asp   | Gly   | Arg   | Ser   | Cys   | Thr   |      |
|       |       |       |       | 270   |       |       |       |       | 275   |       |       |       |       | 280   |       |      |
| GCA   | TCC   | GCG   | ACG   | CAG   | TCC   | TGC   | AAC   | GAC   | CTC   | TGC   | GAG   | CAC   | TTC   | TGC   | GTT   | 1037 |
| Ala   | Ser   | Ala   | Thr   | Gln   | Ser   | Cys   | Asn   | Asp   | Leu   | Cys   | Glu   | His   | Phe   | Cys   | Val   |      |
|       |       |       | 285   |       |       |       |       | 290   |       |       |       |       | 295   |       |       |      |
| CCC   | AAC   | CCC   | GAC   | CAG   | CCG   | GGC   | TCC   | TAC   | TCG   | TGC   | ATG   | TGC   | GAG   | ACC   | GGC   | 1085 |
| Pro   | Asn   | Pro   | Asp   | Gln   | Pro   | Gly   | Ser   | Tyr   | Ser   | Cys   | Met   | Cys   | Glu   | Thr   | Gly   |      |
|       |       | 300   |       |       |       |       | 305   |       |       |       |       | 310   |       |       |       |      |
| TAC   | CGG   | CTG   | GCG   | GCC   | GAC   | CAA   | CAC   | CGG   | TGC   | GAG   | GAC   | GTG   | GAT   | GAC   | TGC   | 1133 |
| Tyr   | Arg   | Leu   | Ala   | Ala   | Asp   | Gln   | His   | Arg   | Cys   | Glu   | Asp   | Val   | Asp   | Asp   | Cys   |      |
|       | 315   |       |       |       |       | 320   |       |       |       |       | 325   |       |       |       |       |      |
| ATA   | CTG   | GAG   | CCC   | AGT   | CCG   | TGT   | CCG   | CAG   | CGC   | TGT   | GTC   | AAC   | ACA   | CAG   | GGT   | 1181 |
| Ile   | Leu   | Glu   | Pro   | Ser   | Pro   | Cys   | Pro   | Gln   | Arg   | Cys   | Val   | Asn   | Thr   | Gln   | Gly   |      |
| 330   |       |       |       |       | 335   |       |       |       |       | 340   |       |       |       |       | 345   |      |
| GGC   | TTC   | GAG   | TGC   | CAC   | TGC   | TAC   | CCT   | AAC   | TAC   | GAC   | CTG   | GTG   | GAC   | GGC   | GAG   | 1229 |
| Gly   | Phe   | Glu   | Cys   | His   | Cys   | Tyr   | Pro   | Asn   | Tyr   | Asp   | Leu   | Val   | Asp   | Gly   | Glu   |      |
|       |       |       |       | 350   |       |       |       |       | 355   |       |       |       |       | 360   |       |      |
| TGT   | GTG   | GAG   | CCC   | GTG   | GAC   | CCG   | TGC   | TTC   | AGA   | GCC   | AAC   | TGC   | GAG   | TAC   | CAG   | 1277 |
| Cys   | Val   | Glu   | Pro   | Val   | Asp   | Pro   | Cys   | Phe   | Arg   | Ala   | Asn   | Cys   | Glu   | Tyr   | Gln   |      |
|       |       |       | 365   |       |       |       |       | 370   |       |       |       |       | 375   |       |       |      |
| TGC   | CAG   | CCC   | CTG   | AAC   | CAA   | ACT   | AGC   | TAC   | CTC   | TGC   | GTC   | TGC   | GCC   | GAG   | GGC   | 1325 |
| Cys   | Gln   | Pro   | Leu   | Asn   | Gln   | Thr   | Ser   | Tyr   | Leu   | Cys   | Val   | Cys   | Ala   | Glu   | Gly   |      |

-continued

|  |  |  | 380 |  |  |  | 385 |  |  |  | 390 |  |  |  |  |
|---|---|---|---|---|---|---|---|---|---|---|---|---|---|---|---|
| TTC Phe 395 | GCG Ala | CCC Pro | ATT Ile | CCC Pro | CAC His | GAG Glu 400 | CCG Pro | CAC His | AGG Arg | TGC Cys | CAG Gln 405 | ATG Met | TTT Phe | TGC Cys | AAC Asn | 1373 |
| CAG Gln 410 | ACT Thr | GCC Ala | TGT Cys | CCA Pro | GCC Ala 415 | GAC Asp | TGC Cys | GAC Asp | CCC Pro | AAC Asn 420 | ACC Thr | CAG Gln | GCT Ala | AGC Ser | TGT Cys 425 | 1421 |
| GAG Glu | TGC Cys | CCT Pro | GAA Glu | GGC Gly 430 | TAC Tyr | ATC Ile | CTG Leu | GAC Asp | GAC Asp 435 | GGT Gly | TTC Phe | ATC Ile | TGC Cys | ACG Thr 440 | GAC Asp | 1469 |
| ATC Ile | GAC Asp | GAG Glu | TGC Cys 445 | GAA Glu | AAC Asn | GGC Gly | GGC Gly | TTC Phe 450 | TGC Cys | TCC Ser | GGG Gly | GTG Val | TGC Cys 455 | CAC His | AAC Asn | 1517 |
| CTC Leu | CCC Pro | GGT Gly 460 | ACC Thr | TTC Phe | GAG Glu | TGC Cys | ATC Ile 465 | TGC Cys | GGG Gly | CCC Pro | GAC Asp | TCG Ser 470 | GCC Ala | CTT Leu | GCC Ala | 1565 |
| CGC Arg 475 | CAC His | ATT Ile | GGC Gly | ACC Thr | GAC Asp 480 | TGT Cys | GAC Asp | TCC Ser | GGC Gly | AAG Lys 485 | GTG Val | GAC Asp | GGT Gly | GGC Gly | GAC Asp | 1613 |
| AGC Ser 490 | GGC Gly | TCT Ser | GGC Gly | GAG Glu | CCC Pro 495 | CCG Pro | CCC Pro | AGC Ser | CCG Pro 500 | ACG Thr | CCC Pro | GGC Gly | TCC Ser | ACC Thr | TTG Leu 505 | 1661 |
| ACT Thr | CCT Pro | CCG Pro | GCC Ala | GTG Val 510 | GGG Gly | CTC Leu | GTG Val | CAT His | TCG Ser 515 | GGC Gly | TTG Leu | CTC Leu | ATA Ile | GGC Gly 520 | ATC Ile | 1709 |
| TCC Ser | ATC Ile | GCG Ala | AGC Ser 525 | CTG Leu | TGC Cys | CTG Leu | GTG Val | GTG Val 530 | GCG Ala | CTT Leu | TTG Leu | GCG Ala | CTC Leu 535 | CTC Leu | TGC Cys | 1757 |
| CAC His | CTG Leu | CGC Arg | AAG Lys 540 | AAG Lys | CAG Gln | GGC Gly | GCC Ala | GCC Ala 545 | AGG Arg | GCC Ala | AAG Lys | ATG Met | GAG Glu 550 | TAC Tyr | AAG Lys | 1805 |
| TGC Cys 555 | GCG Ala | GCC Ala | CCT Pro | TCC Ser | AAG Lys 560 | GAG Glu | GTA Val | GTG Val | CTG Leu | CAG Gln 565 | CAC His | GTG Val | CGG Arg | ACC Thr | GAG Glu | 1853 |
| CGG Arg 570 | ACG Thr | CCG Pro | CAG Gln | AGA Arg | CTC Leu 575 | TGAGCGGCCT | | CCGTCCAGGA | | GCCTGGCTCC | | | | | | 1901 |

GTCCAGGAGC CTGTGCCTCC TCACCCCCAG CTTTGCTACC AAAGCACCTT AGCTGGCATT 1961

ACAGCTGGAG AAGACCCTCC CCGCACCCCC CAAGCTGTTT TCTTCTATTC 2011

( 2 ) INFORMATION FOR SEQ ID NO:54:

( i ) SEQUENCE CHARACTERISTICS:
( A ) LENGTH: 575 amino acids
( B ) TYPE: amino acid
( D ) TOPOLOGY: linear ( i i ) MOLECULE TYPE: protein ( x i ) SEQUENCE DESCRIPTION: SEQ ID NO:54:

| Met 1 | Leu | Gly | Val | Leu 5 | Val | Leu | Gly | Ala | Leu 10 | Ala | Leu | Ala | Gly | Leu 15 | Gly |
| Phe | Pro | Ala | Pro 20 | Ala | Glu | Pro | Gln | Pro 25 | Gly | Gly | Ser | Gln | Cys 30 | Val | Glu |
| His | Asp | Cys 35 | Ser | Ala | Leu | Tyr | Pro 40 | Gly | Pro | Ala | Thr | Phe 45 | Leu | Asn | Ala |
| Ser | Gln | Ile 50 | Cys | Asp | Gly | Leu | Arg 55 | Gly | His | Leu | Met | Thr 60 | Val | Arg | Ser |
| Ser 65 | Val | Ala | Ala | Asp | Val 70 | Ile | Ser | Leu | Leu | Leu 75 | Asn | Gly | Asp | Gly | Gly 80 |

```
Val Gly Arg Arg Arg Leu Trp Ile Gly Leu Gln Leu Pro Pro Gly Cys
                85              90              95

Gly Asp Pro Lys Arg Leu Gly Pro Leu Arg Gly Phe Gln Trp Val Thr
            100             105             110

Gly Asp Asn Asn Thr Ser Tyr Ser Arg Trp Ala Arg Leu Asp Leu Asn
        115             120             125

Gly Ala Pro Leu Cys Gly Pro Leu Cys Val Ala Val Ser Ala Ala Glu
    130             135             140

Ala Thr Val Pro Ser Glu Pro Ile Trp Glu Gln Gln Cys Glu Val
145             150             155                 160

Lys Ala Asp Gly Phe Leu Cys Glu Phe His Phe Pro Ala Thr Cys Arg
                165             170             175

Pro Leu Ala Val Glu Pro Gly Ala Ala Ala Ala Val Ser Ile Thr
            180             185             190

Tyr Gly Thr Pro Phe Ala Ala Arg Gly Ala Asp Phe Gln Ala Leu Pro
        195             200             205

Val Gly Ser Ser Ala Ala Val Ala Pro Leu Gly Leu Gln Leu Met Cys
    210             215             220

Thr Ala Pro Pro Gly Ala Val Gln Gly His Trp Ala Arg Glu Ala Pro
225             230             235                 240

Gly Ala Trp Asp Cys Ser Val Glu Asn Gly Gly Cys Glu His Ala Cys
                245             250             255

Asn Ala Ile Pro Gly Ala Pro Arg Cys Gln Cys Pro Ala Gly Ala Ala
            260             265             270

Leu Gln Ala Asp Gly Arg Ser Cys Thr Ala Ser Ala Thr Gln Ser Cys
        275             280             285

Asn Asp Leu Cys Glu His Phe Cys Val Pro Asn Pro Asp Gln Pro Gly
    290             295             300

Ser Tyr Ser Cys Met Cys Glu Thr Gly Tyr Arg Leu Ala Ala Asp Gln
305             310             315                 320

His Arg Cys Glu Asp Val Asp Asp Cys Ile Leu Glu Pro Ser Pro Cys
                325             330             335

Pro Gln Arg Cys Val Asn Thr Gln Gly Gly Phe Glu Cys His Cys Tyr
            340             345             350

Pro Asn Tyr Asp Leu Val Asp Gly Glu Cys Val Glu Pro Val Asp Pro
        355             360             365

Cys Phe Arg Ala Asn Cys Glu Tyr Gln Cys Gln Pro Leu Asn Gln Thr
    370             375             380

Ser Tyr Leu Cys Val Cys Ala Glu Gly Phe Ala Pro Ile Pro His Glu
385             390             395                 400

Pro His Arg Cys Gln Met Phe Cys Asn Gln Thr Ala Cys Pro Ala Asp
                405             410             415

Cys Asp Pro Asn Thr Gln Ala Ser Cys Glu Cys Pro Glu Gly Tyr Ile
            420             425             430

Leu Asp Asp Gly Phe Ile Cys Thr Asp Ile Asp Glu Cys Glu Asn Gly
        435             440             445

Gly Phe Cys Ser Gly Val Cys His Asn Leu Pro Gly Thr Phe Glu Cys
    450             455             460

Ile Cys Gly Pro Asp Ser Ala Leu Ala Arg His Ile Gly Thr Asp Cys
465             470             475                 480

Asp Ser Gly Lys Val Asp Gly Gly Asp Ser Gly Ser Gly Glu Pro Pro
                485             490             495

Pro Ser Pro Thr Pro Gly Ser Thr Leu Thr Pro Pro Ala Val Gly Leu
```

```
                    500                      505                       510
Val  His  Ser  Gly  Leu  Leu  Ile  Gly  Ile  Ser  Ile  Ala  Ser  Leu  Cys  Leu
          515                      520                      525

Val  Val  Ala  Leu  Leu  Ala  Leu  Leu  Cys  His  Leu  Arg  Lys  Lys  Gln  Gly
     530                      535                      540

Ala  Ala  Arg  Ala  Lys  Met  Glu  Tyr  Lys  Cys  Ala  Ala  Pro  Ser  Lys  Glu
545                      550                      555                      560

Val  Val  Leu  Gln  His  Val  Arg  Thr  Glu  Arg  Thr  Pro  Gln  Arg  Leu
                    565                      570                      575
```

( 2 ) INFORMATION FOR SEQ ID NO:55:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: CDS
        ( B ) LOCATION: 2..58

( x i ) SEQUENCE DESCRIPTION: SEQ ID NO:55:

```
C  CCC  GAC  CAG  CCG  GGC  TCC  TAC  TCG  TGC  ATG  TGC  GAG  ACC  GGC  TAC     46
   Pro  Asp  Gln  Pro  Gly  Ser  Tyr  Ser  Cys  Met  Cys  Glu  Thr  Gly  Tyr
   1                   5                        10                       15

CGG  CTG  GCG  GCC  G                                                            59
Arg  Leu  Ala  Ala
```

( 2 ) INFORMATION FOR SEQ ID NO:56:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Pro  Asp  Gln  Pro  Gly  Ser  Tyr  Ser  Cys  Met  Cys  Glu  Thr  Gly  Tyr  Arg
1                   5                        10                       15

Leu  Ala  Ala
```

( 2 ) INFORMATION FOR SEQ ID NO:57:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: CDS
        ( B ) LOCATION: 2..58
        ( D ) OTHER INFORMATION: /note="mutated bases at 23-25 and 29"

( x i ) SEQUENCE DESCRIPTION: SEQ ID NO:57:

```
C  CCC  GAC  CAG  CCG  GGC  TCC  TAC  AGC  TGC  CTG  TGC  GAG  ACC  GGC  TAC     46
   Pro  Asp  Gln  Pro  Gly  Ser  Tyr  Ser  Cys  Leu  Cys  Glu  Thr  Gly  Tyr
   1                   5                        10                       15

CGG  CTG  GCG  GCC  G                                                            59
Arg  Leu  Ala  Ala
```

( 2 ) INFORMATION FOR SEQ ID NO:58:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: CDS
        ( B ) LOCATION: 1..51
        ( D ) OTHER INFORMATION: /note="Mutated bases at 22-23 and 33"

( x i ) SEQUENCE DESCRIPTION: SEQ ID NO:58:

```
CAG CCG GGC TCC TAC TCG TGC CAG TGC GAG ACT GGC TAC CGG CTG GCG     48
Gln Pro Gly Ser Tyr Ser Cys Gln Cys Glu Thr Gly Tyr Arg Leu Ala
 1               5                  10                  15

GCC G                                                                52
Ala
```

( 2 ) INFORMATION FOR SEQ ID NO:59:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: CDS
        ( B ) LOCATION: 2..58
        ( D ) OTHER INFORMATION: /note="Mutated bases at 29-31"

( x i ) SEQUENCE DESCRIPTION: SEQ ID NO:59:

```
C CCC GAC CAG CCG GGC TCC TAC TCG TGC GCA TGC GAG ACC GGC TAC       46
  Pro Asp Gln Pro Gly Ser Tyr Ser Cys Ala Cys Glu Thr Gly Tyr
   1               5                  10                  15

CGG CTG GCG GCC G                                                    59
Arg Leu Ala Ala
```

( 2 ) INFORMATION FOR SEQ ID NO:60:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: CDS
        ( B ) LOCATION: 1..54

( x i ) SEQUENCE DESCRIPTION: SEQ ID NO:60:

```
CCC CAC GAG CCG CAC AGG TGC CAG ATG TTT TGC AAC CAG ACT GCC TGT     48
Pro His Glu Pro His Arg Cys Gln Met Phe Cys Asn Gln Thr Ala Cys
 1               5                  10                  15

CCA GCC G                                                            55
Pro Ala
```

( 2 ) INFORMATION FOR SEQ ID NO:61:

( i ) SEQUENCE CHARACTERISTICS:

-continued (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:61:

Pro His Glu Pro His Arg Cys Gln Met Phe Cys Asn Gln Thr Ala Cys
 1               5                   10                  15
Pro Ala (2) INFORMATION FOR SEQ ID NO:62:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (primer)

(ix) FEATURE:
        (A) NAME/KEY: CDS
        (B) LOCATION: 1..54
        (D) OTHER INFORMATION: /note="Mutated bases at positions
            21, 24-26"

(xi) SEQUENCE DESCRIPTION: SEQ ID NO:62:

CCC CAC GAG CCG CAC AGG TGT CAA CAG TTT TGC AAC CAG ACT GCC TGT    48
Pro His Glu Pro His Arg Cys Gln Gln Phe Cys Asn Gln Thr Ala Cys
 1               5                   10                  15

CCA GCC G                                                          55
Pro Ala (2) INFORMATION FOR SEQ ID NO:63:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (primer)

(ix) FEATURE:
        (A) NAME/KEY: CDS
        (B) LOCATION: 1..54
        (D) OTHER INFORMATION: /note="Mutated bases at positions
            25-27"

(xi) SEQUENCE DESCRIPTION: SEQ ID NO:63:

CCC CAC GAG CCG CAC AGG TGC CAG GCC TTT TGC AAC CAG ACT GCC TGT    48
Pro His Glu Pro His Arg Cys Gln Ala Phe Cys Asn Gln Thr Ala Cys
 1               5                   10                  15

CCA GCC G                                                          55
Pro Ala